United States Patent
Koizumi et al.

(10) Patent No.: US 10,980,787 B2
(45) Date of Patent: Apr. 20, 2021

(54) DRUG FOR TREATING OR PREVENTING DISORDER CAUSED BY TGF-B SIGNALS, AND APPLICATION THEREOF

(71) Applicant: THE DOSHISHA, Kyoto (JP)

(72) Inventors: Noriko Koizumi, Kyoto (JP); Naoki Okumura, Kyoto (JP)

(73) Assignee: THE DOSHISHA, Kyoto (JP)

( * ) Notice: Subject to any disclaimer, the term of this patent is extended or adjusted under 35 U.S.C. 154(b) by 0 days.

(21) Appl. No.: 16/062,045

(22) PCT Filed: Dec. 22, 2016

(86) PCT No.: PCT/JP2016/005215
§ 371 (c)(1),
(2) Date: Jun. 13, 2018

(87) PCT Pub. No.: WO2017/110093
PCT Pub. Date: Jun. 29, 2017

(65) Prior Publication Data
US 2018/0369220 A1    Dec. 27, 2018

(30) Foreign Application Priority Data
Dec. 24, 2015 (JP) .............................. JP2015-251786

(51) Int. Cl.
| | | |
|---|---|---|
| A61K 31/4439 | (2006.01) | |
| A61P 27/02 | (2006.01) | |
| A61P 43/00 | (2006.01) | |
| A61K 31/17 | (2006.01) | |
| A61K 31/4412 | (2006.01) | |
| A61K 31/4418 | (2006.01) | |
| A61K 31/573 | (2006.01) | |
| A61K 45/06 | (2006.01) | |

(52) U.S. Cl.
CPC .......... *A61K 31/4439* (2013.01); *A61K 31/17* (2013.01); *A61K 31/4412* (2013.01); *A61K 31/4418* (2013.01); *A61K 31/573* (2013.01); *A61K 45/06* (2013.01); *A61P 27/02* (2018.01); *A61P 43/00* (2018.01)

(58) Field of Classification Search
CPC ............ A61K 31/4439; A61K 31/4412; A61K 31/4418; A61K 31/573; A61K 45/06; A61P 27/02; A61P 43/00
See application file for complete search history.

(56) References Cited

U.S. PATENT DOCUMENTS

| | | |
|---|---|---|
| 7,662,389 B2 | 2/2010 | Clark et al. |
| 2005/0119262 A1 | 6/2005 | Wax |
| 2006/0189541 A1 | 8/2006 | Gamache |
| 2008/0119498 A1 | 5/2008 | Kato et al. |
| 2009/0202524 A1 | 8/2009 | Fleenor et al. |
| 2009/0232772 A1 | 9/2009 | Amano et al. |
| 2010/0028328 A1 | 2/2010 | Reiff et al. |
| 2010/0144755 A1 | 6/2010 | Corsi et al. |
| 2010/0209402 A1 | 8/2010 | Koizumi et al. |
| 2015/0044178 A1 | 2/2015 | Kinoshita et al. |
| 2016/0296505 A1 | 10/2016 | Koizumi et al. |
| 2016/0331736 A1 | 11/2016 | Koizumi et al. |

FOREIGN PATENT DOCUMENTS

| | | |
|---|---|---|
| EP | 1 548 008 A1 | 6/2005 |
| EP | 1 669 367 A1 | 6/2006 |
| EP | 1 835 023 | 9/2007 |
| EP | 2 034 838 | 3/2009 |
| EP | 2 799 537 | 11/2014 |
| EP | 3 064 222 A1 | 9/2016 |
| JP | 2006-508169 A | 3/2006 |
| JP | 2006-187281 | 7/2006 |
| JP | 2006-188496 A | 7/2006 |
| JP | 2007-525204 A | 9/2007 |
| JP | 2009-539977 A | 11/2009 |
| JP | 2009-542816 | 12/2009 |
| JP | 2010-513563 A | 4/2010 |
| JP | 2011-518828 A | 6/2011 |
| JP | 2013-520405 A | 6/2013 |
| WO | WO-2004/018430 A1 | 3/2004 |
| WO | WO-2004/060388 A1 | 7/2004 |
| WO | WO-2006/092894 | 9/2006 |
| WO | WO-2007/147103 | 12/2007 |
| WO | WO-2011/101478 A1 | 8/2011 |

(Continued)

OTHER PUBLICATIONS

Shivanna et al. (IOVS, Mar. 2010, 51, 1575-1582) (Year: 2010).*
Kopplin et al. (Molecular Vision, 2010, 16, 1781-1790). (Year: 2010).*
Bruinsma et al., "What does the future hold for the treatment of Fuchs endothelial dystrophy; will 'keratoplasty' still be a valid procedure?," Eye (Lond) Oct. 2013; 27(10):1115-1122.*
Adachi et al., "Contribution of p38 MAPK, NF-KB and glucocorticoid signaling pathways to ER stress-induced increase in retinal endothelial permeability," Archives of Biochemistry and Biophysics, (Jan. 2012) vol. 520,No. 1, pp. 30-35.
Corwin et al., "The unfolded protein response in human corneal endothelial cells following hypothermic storage: Implications of a novel stress pathway," Cryobiology (Apr. 2011) vol. 63, No. 1, pp. 46-55.

(Continued)

*Primary Examiner* — Jared Barsky
(74) *Attorney, Agent, or Firm* — Foley & Lardner LLP

(57) ABSTRACT

Provided is a drug or method for treating or preventing a condition, disorder, or disease of the corneal endothelium caused by transforming growth factor-β (TGF-β) signals, mitochondrial abnormalities, and/or endoplasmic reticulum (ER) associated stress in corneal endothelial cells, using p38 MAP kinase inhibitors. The present invention provides a drug which includes p38 MAP kinase inhibitors, and which is for treating or preventing a condition, disorder, or disease of the corneal endothelium caused by TGF-β signals and/or mitochondrial abnormalities in corneal endothelial cells. In the preferred embodiment, the condition, disorder, or disease of the corneal endothelium is Fuchs' corneal endothelial dystrophy.

4 Claims, 14 Drawing Sheets

(56) References Cited

FOREIGN PATENT DOCUMENTS

| WO | WO-2012/009171 A2 | 1/2012 | |
|---|---|---|---|
| WO | WO-2012/167143 A1 | 12/2012 | |
| WO | WO-2013/100208 A1 | 7/2013 | |
| WO | WO-2013100208 A1 * | 7/2013 | ........... A01N 1/0226 |
| WO | WO-2015/015655 A1 | 2/2015 | |
| WO | WO-2015/064768 A1 | 5/2015 | |
| WO | WO-2015/072580 A1 | 5/2015 | |

OTHER PUBLICATIONS

Huang et al., "Endoplasmic reticulum stress-induced hepatic stellate cell apoptosis through calcium-mediated JNK/P38 MAPK and Calpain/Caspase-12 pathways," Molecular Cellular Biochemistry (Jun. 2014) vol. 394, pp. 1-12.
Kim et al., "p38 Mitogen-Activated Protein Kinase is Involved in Endoplasmic Reticulum Stress-Induced Cell Death and Autophagy in Human Gingival Fibroblasts," Biological & Pharmaceutical Bulletin (2010) vol. 33, No. 4. pp. 545-549.
Shivanna et al., "Barrier Dysfunction of the Corneal Endothelium in Response to TNF-a: Role of p38 MAP Kinase," Investigative Ophthalmology & Visual Science, vol. 51, No. 3, pp. 1575-1582 (Mar. 2010).
Song et al., "Induction of FGF-2 Synthesis by IL-1B in Aqueous Humor through P13-Kinase and p38 in Rabbit Corneal Endothelium," Investigative Ophthalmology & Visual Science vol. 51, No. 2, pp. 822-829 (Feb. 2010).
Awad et al., Growth Regulation via p38 Mitogen-activated Protein Kinase in Developing Liver, The Journal of Biological Chemistry, vol. 275, No. 49, Issue of Dec. 8, pp. 38716-38721 (2000).
Colby, Medical treatment of Fuch's Dystrophy in our lifetime, IOVS, (2013).
Extended European Search Report dated Jul. 17, 2017 in European Appl. 14861468.8 (8 pgs.).
Fuch's-Dystrophy, Medline Plus Article, 2014.
Funaki et al., Smad7 Suppresses the Inhibitory Effect of TGF-beta2 on corneal endothelial cell proliferation and accelerates corneal endothelial wound closure in vitro, Cornea, 22(2): 153-159 (2003).
Huh et al., Distribution of TGF-beta isoforms and signaling intermediates in corneal fibrotic wound repair, Journal of Cellular Biochemistry, 108:476-488,2009 (2009).
International Search Report and Written Opinion issued in PCT/JP2014/080831.
Kaufman, The coreal endothelium in intraocular surgery, Journal of Royal Society of Medicine, vol. 73, Mar. 1980.
Office Action dated Mar. 24, 2020 in U.S. Appl. No. 15/034,710 (US 2016-0331736).
Office Action dated Apr. 26, 2018 in U.S. Appl No. 15/034,710 (US 2016-0331736).
Office Action dated Dec. 18, 2018 in U.S. Appl. No. 15/034,710 (US 2016-0331736).
Okumura et al., The new therapeutic concept of using a Rho kinase inhibitor for the treatment of corneal endothelial dysfunction, Cornea, vol. 30, No. 10, Supplement 1, p. S54-S59, (Oct. 2011).
Okumura et al., Enhancement on Primate Corneal Endothelial Cell Survival in Vitro by a Rock inhibitor, IOVS, (Aug. 2009), vol. 50 , No. 8, p. 3680-3687.
Rajashekhar G. et al., "Role of MMP-9 in the breakdown of barrier integrity of the corneal endothelium in response TNF-a", Experimental Eye Research, Mar. 2014, vol. 122, p. 77-85.
SB203580, Product Catalog, Webpage, SelleckChem.com (2020).
Notice of Allowance dated Jul. 16, 2020 in U.S. Appl. No. 15/034,710 (US 2016-0331736).
Yang et al., "Functional Roles of p38 Mitogen-Activated Protein Kinase in Macrophage-Mediated Inflammatory Responses," Mediators of Inflammation, vol. 2011, Article ID 352371, 13 pages (Mar. 2014).
Azizi et al., "p53-Regulated Increase in Oxidative-Stress-Induced Apoptosis in Fuchs Endothelial Corneal Dystrophy: A Native Tissue model," Investigative Ophthalmology & Visual Science, (Dec. 2011), vol. 52, No. 13, pp. 9291-9297.
Corwin et al., "The unfolded protein response in human corneal endothelial cells following hypothermic storage: Implications of a novel stress pathway," Cryobiology (2011) vol. 63, pp. 46-55.
Kelliher et al., "A cellular model for the investigation of Fuchs' Endothelial Corneal Dystrophy," Experimental Eye Research (2011) vol. 93, pp. 880-888.
Zaniolo et al., "Culture of human corneal endothelial cells isolated from corneas with Fuchs endothelial corneal dystrophy," Experimental Eye Research, vol. 94 (2012) pp. 22-31.

* cited by examiner

DRUG FOR TREATING OR PREVENTING DISORDER CAUSED BY TGF-B SIGNALS, AND APPLICATION THEREOF

CROSS-REFERENCE TO RELATED APPLICATIONS

The present application is the U.S. National Stage of International Application PCT/JP2016/005215, filed Dec. 22, 2016, and claims priority to Japanese Patent Application No. 2015-251786, filed Dec. 24, 2015.

TECHNICAL FIELD

The present invention relates to a technique or method of using a p38 MAP kinase inhibitor for treating or preventing a corneal endothelial condition, disorder, or disease due to at least one of transforming growth factor-β (TGF-β) signal, mitochondrial abnormality, and endoplasmic reticulum stress in corneal endothelial cells, an agent therefor, and a technique of preserving corneal endothelial cells applying said technique.

BACKGROUND ART

Visual information is recognized when light transmitted into the cornea, which is a transparent tissue at the frontmost part of an eye ball, reaches the retina and excites nerve cells of the retina, and a generated electric signal is transmitted through the optic nerve to the visual cortex of the cerebrum. To attain good vision, it is necessary that the cornea is transparent. The transparency of the cornea is retained by maintaining constant water content with pumping and barrier functions of corneal endothelial cells.

Human corneal endothelial cells are present at a density of about 3000 cells per 1 $mm^2$ at birth. Once damaged, human corneal endothelial cells have a very limited ability to regenerate. For example, Fuchs' endothelial corneal dystrophy is a disease causing abnormality in endothelial cells inside the cornea, resulting in edema of the cornea. The cause thereof is unknown. In Fuchs' endothelial corneal dystrophy, extracellular matrix such as collagen is deposited on a part of the back surface of a Descemet's membrane at the back of the cornea, resulting in guttae (Corneal guttae) and hypertrophy of the Descemet's membrane. Guttae (Corneal guttae) and hypertrophy of the Descemet's membrane are the cause of photophobia or blurred vision in Fuchs' endothelial corneal dystrophy patients, which significantly compromises the QOL of the patients. It is understood that there is no effective therapeutic method other than corneal transplant for Fuchs' endothelial corneal dystrophy. However, there is a shortage in cornea donation in Japan, where the number of patients waiting for corneal transplant is about 2600, whereas the number of corneal transplants performed in Japan is approximately 1700 annually.

For Fuchs' endothelial corneal dystrophy, culture (Non Patent Literatures 1 and 3) and immobilization (Non Patent Literature 2) of corneal endothelial cells from Fuchs' corneal dystrophy patients have been reported, but cells suitable for screening of a therapeutic drug or progression preventing drug which maintain the features of the disease, such as overproduction of extracellular matrices, have not been reported. Therefore, there is a limit to the development of a therapeutic drug thereof. Currently, there is no therapeutic drug that is used in clinical practice, so that therapy is reliant on corneal transplant.

Further, Patent Literature 1 discloses a TGF-β1 inhibitor peptide for treating fibrillization and/or opacity of corneas. Patent Literature 2 discloses antibodies that bind to TGF-β1, 2, or 3. Patent Literature 3 discloses that an Nrf2 agonist or activator can be used in the therapy of corneal endothelial disorders. Patent Literature 4 discloses a peptide, which can bind to a transforming growth factor-β1 (TGF-β1) and be a potent bioactive inhibitor of bioactivity of TGF-β1 by directly binding to a cytokine. Patent Literature 5 discloses a scar formation suppressant comprising a BMP-7 polypeptide. Patent Literature 6 describes, in general terms, corneal disorders as diseases on which TGF-β inhibitory action is therapeutically or prophylactically effective.

Corneal endothelial diseases also have a relationship with endoplasmic reticulum stress. Non Patent Literature 4 is a document directed to basic research on the relationship between human corneal endothelial cells and endoplasmic reticulum stress. Patent Literature 7 describes that corneal endothelial diseases associated with endoplasmic reticulum stress due to TGF-β can be treated.

CITATION LIST

Patent Literature

[PTL 1] Japanese National Phase PCT Laid-open Publication No. 2013-520405
[PTL 2] International Publication No. WO 2012/167143
[PTL 3] International Publication No. WO 2012/009171
[PTL 4] Japanese National Phase PCT Laid-open Publication No. 2007-525204
[PTL 5] Japanese National Phase PCT Laid-open Publication No. 2006-508169
[PTL 6] International Publication No. WO 2004/018430
[PTL 7] International Publication No. WO 2015/064768

Non Patent Literature

[NPL 1] Zaniolo K, et al. Exp Eye Res.; 94 (1): 22-31. 2012
[NPL 2] Azizi B, et al. Invest Ophthalmol Vis Sci. 2; 52 (13): 9291-9297. 2011
[NPL 3] Kelliher C. et al. Exp Eye Res Vol. 93 (6), 880-888, 2011
[NPL 4] William L. Corwin et al., Cryobiology: Vol. 63, No. 1, 46-55 (2011)

SUMMARY OF INVENTION

Solution to Problem

The inventors have completed the present invention by discovering that TGF-β signal causes a disorder by using an agent such as transforming growth factor-β 2 (TGF-β2), and discovering that such a disorder is surprisingly treatable with a p38 MAP kinase inhibitor. The inventors have also discovered that mitochondrial abnormalities can be healed with a p38 MAP kinase inhibitor. The present invention has been completed by discovering the application of a p38 MAP kinase inhibitor for use in treating or preventing corneal endothelial disorders (especially corneal endothelial disorders in Fuchs' endothelial corneal dystrophy) due to a transforming growth factor-β (TGF-β) signal and/or mitochondrial abnormality. The inventors have also discovered that a p38 MAP inhibitor suppresses cell damage due to cryopreservation of corneal endothelial cells.

In addition, the inventors have discovered that a p38 MAP kinase inhibitor suppresses endoplasmic reticulum (ER)

associated stress induced by an unfolded protein, and a p38 MAP kinase inhibitor can treat or prevent a corneal endothelial disorder or the like due to endoplasmic reticulum (ER) associated stress.

The present invention therefore provides, for example, the following items.

(Item 1)

A medicament for use in treating or preventing a corneal endothelial condition, disorder, or disease due to at least one of a transforming growth factor-β (TGF-β) signal and a mitochondrial abnormality in corneal endothelial cells, comprising a p38 MAP kinase inhibitor.

(Item 2)

The medicament of item 1, wherein the condition, disorder, or disease is associated with a TGF-β signal and a mitochondrial abnormality.

(Item 3)

The medicament of item 1 or 2, wherein the mitochondrial abnormality is selected from one or more of a decrease in mitochondrial membrane potential, a morphological abnormality of mitochondria, or a decrease in mitochondrial biosynthesis.

(Item 4)

The medicament of any one of items 1 to 3, wherein the condition, disorder, or disease is a condition, disorder, or disease in Fuchs' endothelial corneal dystrophy.

(Item 5)

The medicament of item 4, wherein the medicament prevents the progression of Fuchs' endothelial corneal dystrophy by suppressing a decrease in mitochondrial membrane potential of corneal endothelial cells in Fuchs' endothelial corneal dystrophy.

(Item 6)

The medicament of any one of items 1 to 5, wherein the p38 MAP kinase inhibitor comprises at least one selected from the group consisting of 4-(4-fluorophenyl)-2-(4-methylsulfinylphenyl)-5-(4-pyridyl)-1H-imidazole (SB-203580), 1-(carbamoyl-6-(2,4-difluorophenyl)pyridin-2-yl)-1-(2,6-difluorophenyl)urea (VX-702), and 3-[3-bromo-4-[(2,4-difluorophenyl)methoxy]-6-methyl-2-oxopyridin-1-yl]-N,4-dimethylbenzamide (PH797804).

(Item 7)

The medicament of item 6, wherein the p38 MAP kinase inhibitor comprises 4-(4-fluorophenyl)-2-(4-methylsulfinylphenyl)-5-(4-pyridyl)-1H-imidazole (SB203580) at a concentration of about 3 μM to about 30 μM.

(Item 8)

The medicament of item 6, wherein the p38 MAP kinase inhibitor comprises 1-(carbamoyl-6-(2,4-difluorophenyl)pyridin-2-yl)-1-(2,6-difluorophenyl)urea (VX-702) at a concentration of about 1 μM to about 10 μM.

(Item 9)

The medicament of item 6, wherein the p38 MAP kinase inhibitor comprises 3-[3-bromo-4-[(2,4-difluorophenyl)methoxy]-6-methyl-2-oxopyridin-1-yl]-N,4-dimethylbenzamide (PH797804) at a concentration of about 0.3 μM to about 3 μM.

(Item 10)

A composition for preservation of corneal endothelial cells or culturing after preservation, comprising a p38 MAP kinase inhibitor.

(Item 11)

The composition of item 10, wherein the preservation is cryopreservation.

(Item 12)

The medicament or composition of any one of items 1 to 11, wherein the p38 MAP kinase inhibitor is water-soluble.

(Item 13)

The medicament of any one of items 1 to 9, wherein the p38 MAP kinase inhibitor is provided as an eye drop.

The present invention also provides, for example, the following items.

(Item X1)

A medicament for use in treating or preventing a corneal endothelial condition, disorder, or disease due to at least one of a transforming growth factor-β (TGF-β) signal and a mitochondrial abnormality in corneal endothelial cells, comprising a p38 MAP kinase inhibitor.

(Item X2)

The medicament of item X1, wherein the condition, disorder, or disease is associated with a TGF-β signal and a mitochondrial abnormality.

(Item X3)

The medicament of item X1 or X2, wherein the mitochondrial abnormality is selected from one or more of a decrease in mitochondrial membrane potential, a morphological abnormality of mitochondria, or a decrease in mitochondrial biosynthesis.

(Item X4)

The medicament of any one of items X1 to X3, wherein the condition, disorder, or disease is a condition, disorder, or disease in Fuchs' endothelial corneal dystrophy.

(Item X5)

The medicament of item X4, wherein the medicament prevents the progression of Fuchs' endothelial corneal dystrophy by suppressing a decrease in mitochondrial membrane potential of corneal endothelial cells in Fuchs' endothelial corneal dystrophy.

(Item X6)

The medicament of any one of items X1 to X5, wherein the p38 MAP kinase inhibitor comprises at least one selected from the group consisting of 4-(4-fluorophenyl)-2-(4-methylsulfinylphenyl)-5-(4-pyridyl)-1H-imidazole (SB-203580), 1-(carbamoyl-6-(2,4-difluorophenyl)pyridin-2-yl)-1-(2,6-difluorophenyl)urea (VX-702), and 3-[3-bromo-4-[(2,4-difluorophenyl)methoxy]-6-methyl-2-oxopyridin-1-yl]-N,4-dimethylbenzamide (PH797804).

(Item X7)

The medicament of item X6, wherein the p38 MAP kinase inhibitor comprises 4-(4-fluorophenyl)-2-(4-methylsulfinylphenyl)-5-(4-pyridyl)-1H-imidazole (SB203580) at a concentration of about 3 μM to about 30 μM.

(Item X8)

The medicament of item X6, wherein the p38 MAP kinase inhibitor comprises 1-(carbamoyl-6-(2,4-difluorophenyl)pyridin-2-yl)-1-(2,6-difluorophenyl)urea (VX-702) at a concentration of about 1 μM to about 10 μM.

(Item X9)

The medicament of item X6, wherein the p38 MAP kinase inhibitor comprises 3-[3-bromo-4-[(2,4-difluorophenyl)methoxy]-6-methyl-2-oxopyridin-1-yl]-N,4-dimethylbenzamide (PH797804) at a concentration of about 0.3 μM to about 3 μM.

(Item X10)

A composition for preservation of corneal endothelial cells or culturing after preservation, comprising a p38 MAP kinase inhibitor.

(Item X11)

The composition of item X10, wherein the preservation is cryopreservation.

(Item X12)

A medicament for use in treating or preventing a corneal endothelial condition, disorder, or disease due to endoplasmic reticulum (ER) associated stress in corneal endothelial cells, comprising a p38 MAP kinase inhibitor.

(Item X13)

The medicament of item X12, wherein the condition, disorder, or disease is due to an abnormality in folding of a protein.

(Item X14)

The medicament of item X12 or X13, wherein the condition, disorder, or disease is a condition, disorder, or disease associated with endoplasmic reticulum (ER) associated stress among damage to corneal endothelial cells in Fuchs' endothelial corneal dystrophy, corneal endothelial disorder, decreased corneal endothelial density, guttae formation, hypertrophy of the Descemet's membrane, hypertrophy of a cornea, turbidity, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, and edema of the corneal stroma, corneal epithelial erosion, and angiogenesis.

(Item X15)

A medicament for use in treating or preventing a corneal endothelial condition, disorder, or disease due to at least one of a transforming growth factor-β (TGF-β) signal, a mitochondrial abnormality, and endoplasmic reticulum (ER) associated stress in corneal endothelial cells, comprising a p38 MAP kinase inhibitor.

(Item X16)

The medicament of item X15, wherein the condition, disorder, or disease is selected from the group consisting of damage to corneal endothelial cells in Fuchs' endothelial corneal dystrophy, corneal endothelial disorder, decreased corneal endothelial density, and edema of the corneal stroma, corneal epithelial edema, corneal epithelial erosion, turbidity in corneal stroma, and angiogenesis as a result thereof.

(Item X17)

The medicament of item X15 or X16, wherein the condition, disorder, or disease comprises Fuchs' endothelial corneal dystrophy.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description, as needed.

Advantageous Effects of Invention

The present invention provides a medicament that can treat or prevent a disorder or disease due to a transforming growth factor-β (TGF-β) signal and/or a disease due to a mitochondrial abnormality in Fuchs' endothelial corneal dystrophy or the like, comprising a p38 MAP kinase inhibitor. The present invention also provides a medicament that can treat or prevent a corneal endothelial disorder or the like due to endoplasmic reticulum (ER) associated stress, comprising a p38 MAP kinase inhibitor. The present invention further provides a composition for preserving corneal endothelial cells or a composition for promoting the growth of corneal endothelial cells, comprising a p38 MAP kinase inhibitor.

μM). As shown, it was observed that a p38 MAPK inhibitor did not suppress smad2 and smad3 that are downstream TGF-3 signaling. The cell damage suppressing effect of a p38 MAPK inhibitor in a corneal endothelial disorder model of Fuchs' endothelial corneal dystrophy is not due to suppression of TGF-β signals.

Figure 11:
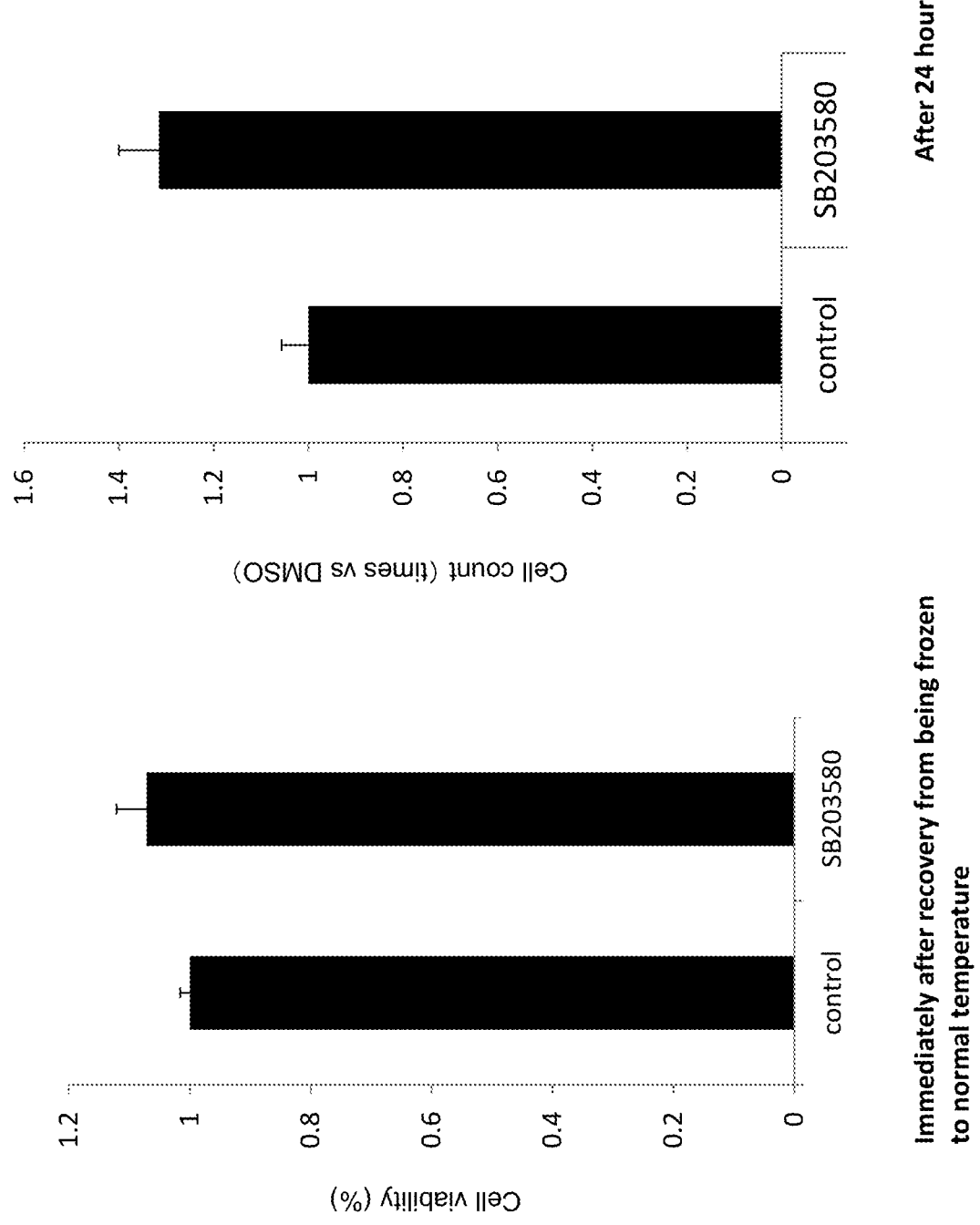

FIG. 11 shows a graph of the cell count after 24 hours from thawing cryopreserved corneal endothelial cells. The vertical axis indicates the ratio of cell count to the control group. The left bar shows the control group, and the right bar shows SB203580.

Figure 12:
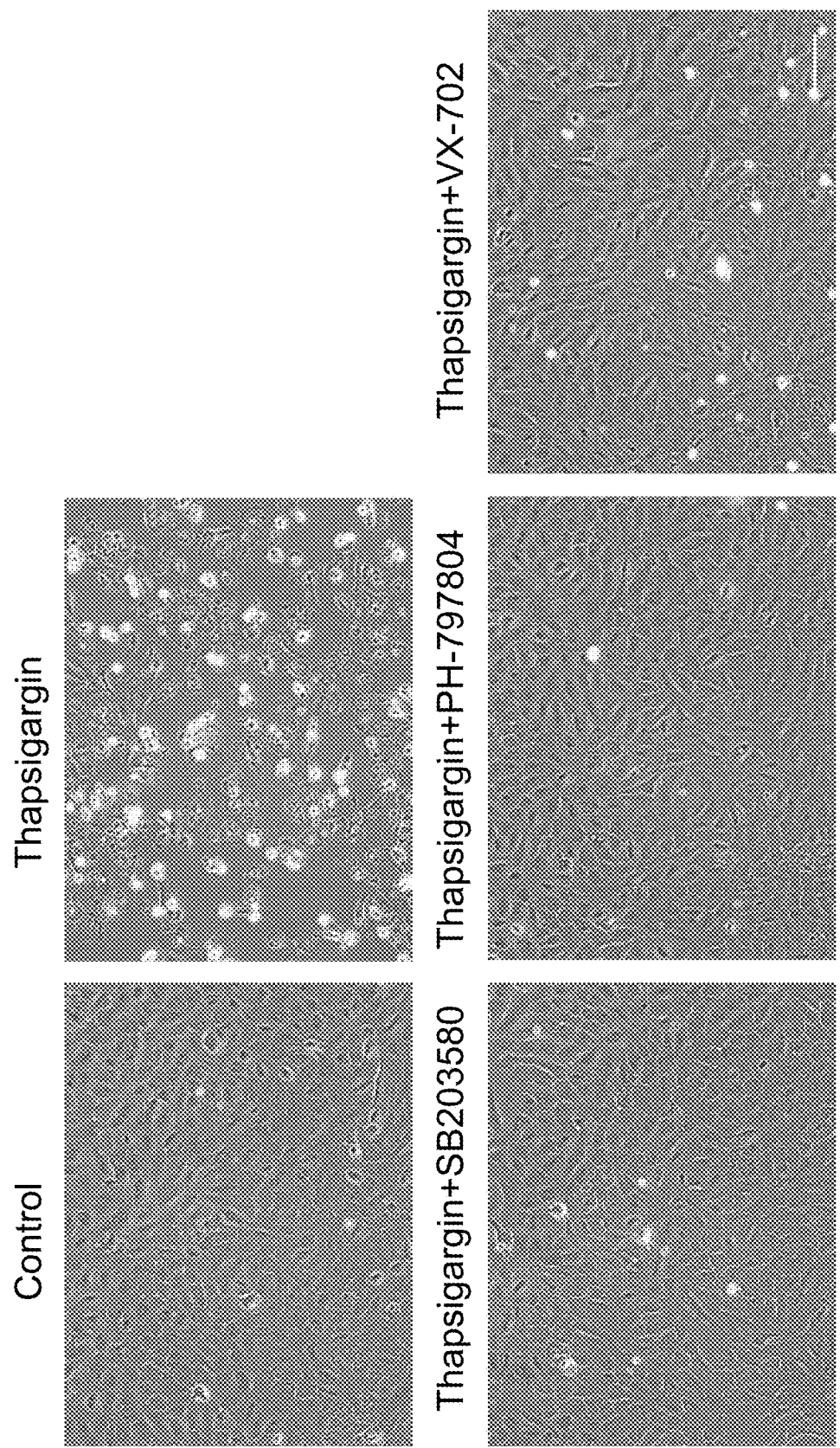

FIG. 12 shows pictures from a phase differential microscope of immobilized human corneal endothelial cells cultured by stimulating immobilized human corneal endothelial cells pretreated with each p38 MAP kinase inhibitor with thapsigargin. (Top panel shows, from the left, control and thapsigargin. The bottom panel shows, from the left, thapsigargin+SB203580 (10 μM), thapsigargin+PH-797804 (1 μM), and thapsigargin+VX-702 (3 μM).

Figure 13:
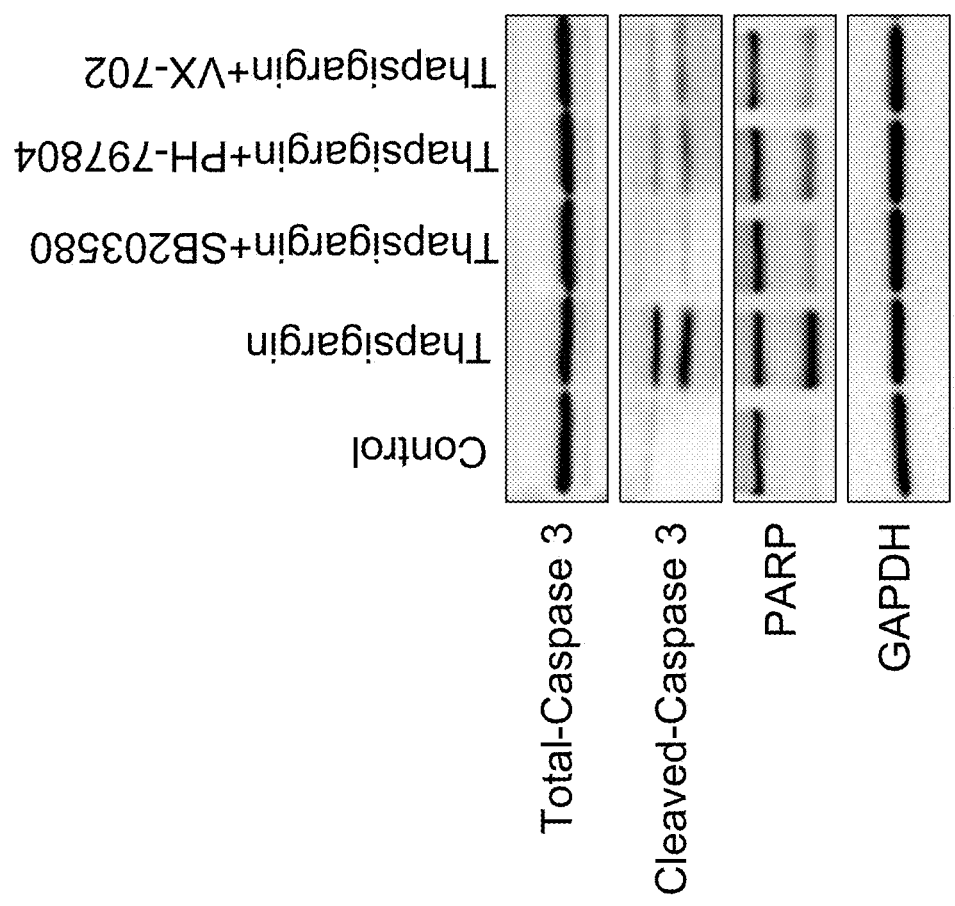

FIG. 13 shows results of western blot on caspase, PARP, and GAPDH. The picture shows, from the left lane, iFECD (control), iFECD+thapsigargin, iFECD+thapsigargin+SB203580 (10 μM), iFECD+thapsigargin+PH-797804 (1 μM), and iFECD+thapsigargin+VX-702 (3 μM).

Figure 14:
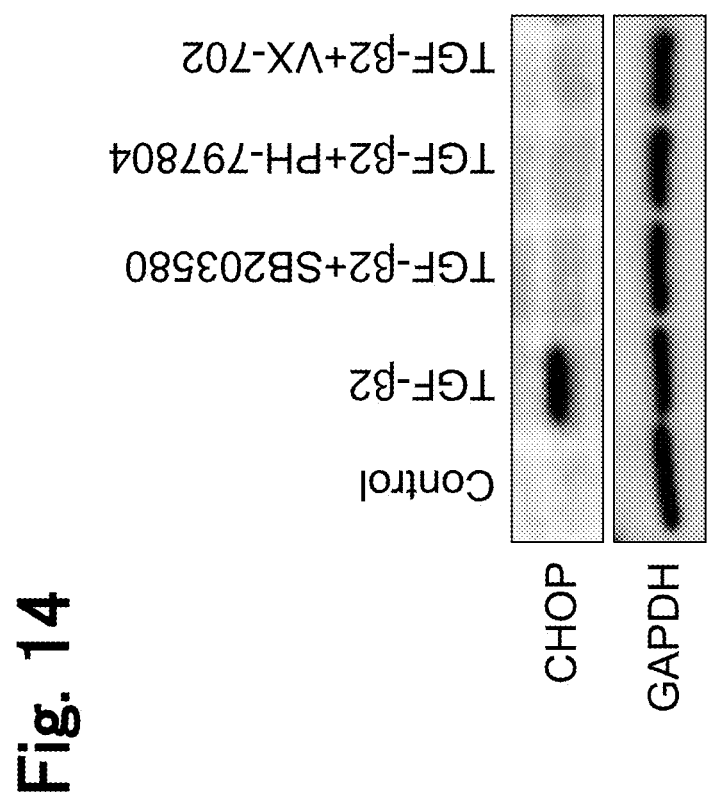

FIG. 14 shows results of western blot on CHOP and GAPDH. The picture shows, from the left lane, iFECD (control), iFECD+TGF-β2, iFECD+TGF-β2+SB203580 (10 μM), iFECD+TGF-β2+PH-797804 (1 μM), and iFECD+TGF-β2+VX-702 (3 μM).

DESCRIPTION OF EMBODIMENTS

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definition

As used herein, "cell mitogen factor (mitogen) activated protein (MAP) kinase" is a mitogen activated protein (MAP) phosphorylating enzyme, which is a part of the serine/threonine kinase family. MAP kinases are from the serine/threonine protein group, which is activated in response to various extracellular stimulations and mediates signaling from a cell surface to a nucleus. MAP kinases are also called extracellular signal-regulated protein kinases or ERK and are terminal enzymes in a 3 kinase cascade. In a related context, a repeat of a 3 kinase cascade for a divided signaling pathway leads to the concept of a MAP kinase pathway as a modular multifunctional signaling element sequentially acting in one pathway, which is characterized in that each enzyme is phosphorylated whereby the next member in the sequence is activated. In this manner, a standard MAP kinase module consists of three protein kinases. In other words, a certain MAP kinase kinase (or MEKK) activates a certain MAP kinase kinase (or V MEK), which activates a certain MAPK/ERK enzyme in order. MAPK/ERK, JNK (c-jun amino terminal protein kinase (or SAPK)) and p38 cascades each consists of three enzyme modules including an MEKK, MEK and ERK, or a MAP kinase superfamily member. When various extracellular signals bind with their respective cell surface receptor, an initial event is triggered, and then the signal is transmitted inside the cells, where an appropriate cascade is activated.

A MAP kinase is a mitogen activated protein kinase (or ERK) super family having a TXY consensus sequence in a catalytic core. ERK1/2, p38HOG, and JNK/SAPK are related in parallel pathways, but are separate terminal enzymes.

Sebolt-Leopold et al., Nat. Med., 5(7): 810-6 (July, 1999) describes an in vitro cascade assay system for identifying a small molecule inhibitor of a MAP kinase (MAPK) pathway. Glutathione-S-transferase (GST)-MEK1 and GST-MAPK fusion proteins prepared from microbial cells were used in this assay system for sequential phosphorylation of MEK1 into MAPK or MBP (myelin basic protein). PD184352 [2-(2-chloro-4-iodine-phenylamino)-N-cyclopropyl-methoxy-3,4-difluoro-benzamide] that directly inhibits MEK1 has also been found.

As used herein, a "p38 MAP kinase inhibitor (also referred to as "p38 MAPK inhibitor")" refers to any agent that inhibits signaling of a MAP kinase associated with p38. Thus, a p38 MAP kinase inhibitor relates to a compound that targets and decreases or inhibits a p38-MAP kinase, which is a MAP kinase family member. It is preferable that a p38 MAP kinase inhibitor is water-soluble. This is because, if the p38 MAP kinase inhibitor is not water soluble, it may be necessarily to use a solvent that is less likely to be compatible to the body. Whether or not a p38 MAP kinase inhibitor is water soluble can be classified based on the definition of solubility in the pharmacopoeia. In other words, the amount of solvent required to dissolve 1 g or 1 mL of solute is defined as extremely readily dissolvable: less than 1 mL; readily dissolvable: 1 mL or greater and less than 10 mL; somewhat readily dissolvable: 10 mL or greater and less than 30 mL; somewhat difficult to dissolve: 30 mL or greater and less than 100 mL; difficult to dissolve: 100 mL or greater and less than 1000 mL; very difficult to dissolve: 1000 mL or greater and less than 10000 mL; and hardly dissolvable: 10000 mL or greater. Solubility is similarly assessed herein. Water solubility is understood to mean that a substance with any solubility can be used, as long as an effective amount thereof can be dissolved when water is used as a solvent. For instance, 4-(4-fluorophenyl)-2-(4-methylsulfinylphenyl)-5-(4-pyridyl)-1H-imidazole (SB-203580) is considered soluble into methanol, but difficult to dissolve into water, while a hydrochloride of 4-(4-fluorophenyl)-2-(4-methylsulfinylphenyl)-5-(4-pyridyl)-1H-imidazole (SB203580) is considered soluble into water and is classified as water-soluble. Such a water-soluble component is advantageously used as an eye drop.

P38 is a mammalian MAP kinase super family member, which is activated by stress, ultraviolet ray, and inflammatory cytokine. P38 has a TGY consensus sequence in a catalytic core.

Abnormally regulated kinases have been gradually recognized as the main pathological cause of many diseases, especially proliferative and inflammatory disorders. One of the carcinogenic genes first identified in a cancer region was for epithelial growth factor receptor kinases (EGFR). Excessive expression thereof is associated with lung, breast, brain, prostate, GI and ovarian cancer. For example, structural activation of a MAP kinase is associated with primary tumor from numerous cancer cell lineages (pancreas, large intestine, lung, ovary, and kidney) and various human organs (kidney, large intestine, and lung) (Hoshino et al., Oncogene, 18(3): 813-22 (Jan. 1999)). Furthermore, p38 MAP kinases regulate the production of two cytokines associated with onset and progression of inflammation, i.e., TNFα and IL-1.

Besides VX-745 (Vertex Pharmaceuticals Inc.), p38 MAP kinase inhibitors that can be used in the present invention are not particularly limited, as long as it is a compound having p38 MAP kinase inhibiting activity, including the compounds described in patent documents such as Japanese Laid-Open Publication No. 2002-97189, Japanese National Phase PCT Laid-open Publication No. 2000-503304, Japanese National Phase PCT Laid-open Publication No. 2001-522357, Japanese National Phase PCT Laid-open Publication No. 2003-535023, Japanese National Phase PCT Laid-open Publication No. 2001-506266, Japanese National Phase PCT Laid-open Publication No. 9-508123, International Publication No. WO 01/56553, International Publication No. WO 93/14081, International Publication No. WO 01/35959, International Publication No. WO 03/68229, International Publication No. WO 03/85859, Japanese National Phase PCT Laid-open Publication No. 2002-534468, Japanese National Phase PCT Laid-open Publication No. 2001-526222, Japanese National Phase PCT Laid-open Publication No. 2001-526223, U.S. Pat. No. 6,344,476, International Publication No. WO 03/99811, International Publication No. WO 03/99796, Japanese National Phase PCT Laid-open Publication No. 2004-506042, International Publication No. WO 04/60286, Japanese National Phase PCT Laid-open Publication No. 2002-363179, Japanese National Phase PCT Laid-open Publication No. 2004-107358, U.S. Pat. Nos. 5,670,527, 6,096,753, International Publication No. WO 01/42189 and International Publication No. WO 00/31063, preferably 4-(4-fluorophenyl)-2-(4-hydroxyphenyl)-5-(4-pyridyl)-1H-imidazole (SB-202190), trans-4-[4-(4-fluorophenyl)-5-(2-methoxy-4-pyrimidinyl)-1H-imidazole-1-yl]cyclohexanol (SB-239063), 4-(4-fluorophenyl)-2-(4-methylsulfinylphenyl)-5-(4-pyridyl)-1H-imidazole (SB-203580), 4-(4-fluorophenyl)-5-(2-methoxypyrimidine-4-yl)-1-(piperidine-4-yl)imidazole (SB-242235), 4-(4-fluorophenyl)-2-(4-hydroxy-1-butynyl)-1-(3-phenylpropyl)-5-(4-pyridyl)imidazole (RWJ-67657), 4-(4-fluorophenyl)-1-(piperidine-4-yl)-5-(4-pyridyl)imidazole (HEP-689), (S)-2-(2-amino-3-phenylpropylamino)-1-methyl-5-(2-naphthyl)-4-(4-pyridyl)pyrimidine-6-one (AMG-548), 2-chloro-4-(4-fluoro-2-methylanilino)-2'-methylbenzophenone (EO-1606), 3-(4-chlorophenyl)-5-(1-hydroxyacetylpiperidine-4-yl)-4-(pyrimidine-4-yl)pyrazole (SD-06), 5-(2,6-dichlorophenyl)-2-(2,4-difluorophenylthio)pyrimido[3,4-b]pyridazine-6-one (VX-745), 4-acetylamino-N-tert-butylbenzamide (CPI-1189), N-[3-tert-butyl-1-(4-methylphenyl)pyrazole-5-yl]-N'-[4-(2-morpholinoethoxy)-1-naphthyl]urea (Doramapimod), 2-benzamide-4-[2-ethyl-4-(3-methylphenyl)thiazole-5-yl]pyridine (TAK-715), SCIO-469, 1-(carbamoyl-6-(2,4-difluorophenyl)pyridine-2-yl)-1-(2,6-difluorophenyl)urea (VX-702; 2-(2,4-difluorophenyl)-6-(1-(2,6-difluorophenyl) ureido)nicotinamide), GSK-681323, PS-540446, SC-80036, AVE-9940, RO-320-1195, 1-(1,3-dihydroxyprop-2-yl)-4-(4-fluorophenyl)-5-[2-phenoxypyrimidine-4-yl]imidazole (SB-281832, 2-[5-({4-[(4-fluorophenyl)methyl]piperidine-1-yl}carbonyl)-6-methoxy-1-methyl-1H-indole-3-yl]-N,N'-dimethyl-2-oxoacetamide (SCIO-323), 2-(5-tert-butyl-2-m-tolyl-2H-pyrazole-3-yl)-2-hydroxyimide-N-[4-(2-morpholine-4-yl-ethoxy)-naphthalene-1-yl]-acetamide (KC-706), N,N'-bis[3,5-bis[1-(2-amidinohydrazono)ethyl]phenyl]decandiamide, N,N'-bis[3,5-bis[1-[2-(aminoiminomethyl)hydrazono]ethyl]phenyl]decandiamide (Semapimod), 3-(3-bromo-4-((2,4-difluorobenzyl)oxy)-6-methyl-2-oxopyridine-1(2H)-yl)-N,4-dimethylbenzamide (PH-797804), and 5-(2-(tert-butyl)-5-(4-fluorophenyl)-1H-imidazole-4-yl)-3-neopentyl-3H-imidazo[4,5-b]pyridine-2-amine (LY2228820).

Furthermore, Tocris Cookson (St Louis, USA) provides various MAP kinase inhibitors exemplified at http://www.tocris.com/. For instance, SB202190 (4-[4-(4-fluorophenyl)-5-(4-pyridinyl)-1H-imidazole-2-yl]phenol) is a highly selective, potent, and cell permeable p38 MAP kinase inhibitor (SmithKline Beecham, plc) (Jiang et al., J. Biol. Chem, 271: 17920 (1996); Frantz et al., Biochemistry, 37: 138-46 (1998); Nemoto et al., J. Biol. Chem., 273: 16415 (1998); and Davies et al., Biochem. J., 351:95 (2000)). Further, anisomycin ((2R,3S,4S)-2-[(4-methoxyphenyl)methyl]-3,4-pyrrolidinediol-3-acetate) is a protein synthesis inhibitor (blocks translation). This is a potent activator of stress activated protein kinases (JNK/SAPK) and p38 MAP kinases, acting as a potent signaling agonist that selectively induces homologous desensitization induced by an immediate early gene (c-fos, fosB, c-jun, junB, and junD). PD98059 (2-(2-amino-3-methoxyphenyl)-4H-1-benzopyran-4-one) is a specific inhibitor of a mitogen activated protein kinase kinase (MAPKK) (Pfizer=Warner-Lambert Company). SB203580 (4-[5-(4-fluorophenyl)-2-[4-(methylsulfonyl)phenyl]-1H-imidazole-4-yl]pyridine) is a highly selective inhibitor of p38 mitogen activated protein kinases (SmithKline Beecham, plc). It is demonstrated that interleukin-2-derived T cell proliferation, cyclooxygenase-1 and -2 and thromboxane synthase are inhibited. SB203580 hydrochloride (4-[5-(4-fluorophenyl)-2-(4-(methylsulfonyl)phenyl)-1H-imidazole-4-yl]pyridine) compound is a water-soluble salt of a highly selective p38 mitogen activated protein kinase inhibitor. It is demonstrated that interleukin-2-derived T cell proliferation, cyclooxygenase-1 and -2 and thromboxane synthase are inhibited. U0126 (1,4-diamino-2,3-dicyano-1,4-bis[2-aminophenylthio]butadiene) is a potent and selective non-competitive inhibitor of MAP kinase kinase.

An example of a preferred p38 MAP kinase inhibitor includes, but is not limited to, SB203580 4-[4-(4-fluorophenyl)-2-(4-methylsulfinylphenyl)-1H-imidazole-5-yl]pyridine).

Other examples of p38 MAP kinase inhibitors that can be used in the present invention include neutralizing antibodies against p38 MAP kinases, compounds inhibiting the activity of p38 MAP kinases, compounds inhibiting transcription of a gene encoding a p38 MAP kinase (e.g., antisense nucleic acids, RNAi, ribozymes), peptides, and compounds with a plant component or the like (e.g., polyphenol, flavonoid, glycoside). A concentration used is for example about 50 nmol/L-100 µmol/L, and is generally about 0.001-100 µmol/L, preferably about 0.01-75 µmol/L, about 0.05-50 µmol/L, about 1-10 µmol/L, about 0.01-10 µmol/L, about 0.05-10 µmol/L, about 0.075-10 µmol/L, about 0.1-10 µmol/L, about 0.5-10 µmol/L, about 0.75-10 µmol/L, about 1.0-10 µmol/L, about 1.25-10 µmol/L, about 1.5-10 µmol/L, about 1.75-10 µmol/L, about 2.0-10 µmol/L, about 2.5-10 µmol/L, about 3.0-10 µmol/L, about 4.0-10 µmol/L, about 5.0-10 µmol/L, about 6.0-10 µmol/L, about 7.0-10 µmol/L, about 8.0-10 µmol/L, about 9.0-10 µmol/L, about 0.01-50 µmol/L, about 0.05-5.0 µmol/L, about 0.075-5.0 µmol/L, about 0.1-5.0 µmol/L, about 0.5-5.0 µmol/L, about 0.75-5.0 µmol/L, about 1.0-5.0 µmol/L, about 1.25-5.0 µmol/L, about 1.5-5.0 µmol/

L, about 1.75-5.0 µmol/L, about 2.0-5.0 µmol/L, about 2.5-5.0 µmol/L, about 3.0-5.0 µmol/L, about 4.0-5.0 µmol/L, about 0.01-3.0 µmol/L, about 0.05-3.0 µmol/L, about 0.075-3.0 µmol/L, about 0.1-3.0 µmol/L, about 0.5-3.0 µmol/L, about 0.75-3.0 µmol/L, about 1.0-3.0 µmol/L, about 1.25-3.0 µmol/L, about 1.5-3.0 µmol/L, about 1.75-3.0 µmol/L, about 2.0-3.0 µmol/L, about 0.01-1.0 µmol/L, about 0.05-1.0 µmol/L, about 0.075-1.0 µmol/L, about 0.1-1.0 µmol/L, about 0.5-1.0 µmol/L, about 0.75-1.0 µmol/L, about 0.09-35 µmol/L, about 0.09-3.2 µmol/L, and more preferably about 0.05-1.0 µmol/L, about 0.075-1.0 µmol/L, about 0.1-1.0 µmol/L, about 0.5-1.0 µmol/L, and about 0.75-1.0 µmol/L, but is not limited thereto.

Antisense nucleic acids used in the present invention may inhibit the expression and/or function of a gene (nucleic acid) encoding a member of a signaling pathway of the p38 MAP kinase discussed above or the like by any of the above-described action. As one embodiment, designing an antisense sequence complementary to an untranslated region near the 5' end of mRNA of a gene encoding the aforementioned p38 MAP kinase or the like is considered effective for inhibiting translation of a gene. Further, a sequence that is complementary to an untranslated region of 3' or a coding region can also be used. In this manner, antisense nucleic acids utilized in the present invention include not only a translation region of a gene encoding the aforementioned p38 MAP kinase or the like, but also nucleic acids comprising an antisense sequence of a sequence of an untranslated region. An antisense nucleic acid to be used is linked downstream of a suitable promoter, and preferably a sequence comprising a transcription termination signal is linked to the 3' side. A nucleic acid prepared in this manner can be transformed into a desired animal (cell) by using a known method. A sequence of an antisense nucleic acid is preferably a sequence that is complementary to a gene encoding a p38 MAP kinase or the like of the animal (cell) to be transformed or a portion thereof. However, such a sequence does not need to be fully complementary, as long as gene expression can be effectively suppressed. A transcribed RNA preferably has complementarity that is 90% or greater, and most preferably 95% or greater, with respect to a transcript of a target gene. In order to effectively inhibit the expression of a target gene using an antisense nucleic acid, it is preferable that the length of the antisense nucleic acid is at least 12 bases and less than 25 bases. However, the antisense nucleic acid of the present invention is not necessarily limited to this length. For example, the length may be 11 bases or less, 100 bases or more, or 500 bases or more. An antisense nucleic acid may be composed of only DNA, but may comprise a nucleic acid other than DNAs, such as a locked nucleic acid (LNA). As one embodiment, an antisense nucleic acid used in the present invention may be an LNA containing antisense nucleic acid comprising LNA at the 5' end or LNA at the 3' end. In an embodiment using an antisense nucleic acid in the present invention, the antisense sequence can be designed based on a nucleic acid sequence of a p38 MAP kinase or the like by using the method described in, for example, Hirashima and Inoue, Shin-seikagaku Jikkenn Kouza 2 [*New Biochemical Experiment Course* 2] Kakusan IV Idenshi no Fukusei to Hatsugen [*Duplication and Expression of Gene of Nucleic Acid IV*], Ed. by the Japanese Biochemical Society, Tokyo Kagaku Dojin, 1993, 319-347.

Expression of p38 MAP kinases or the like can also be inhibited by utilizing a ribozyme or DNA encoding a ribozyme. A ribozyme refers to an RNA molecule having catalytic activity. While there are ribozymes with various activities, a study focusing on especially ribozymes as an enzyme for cleaving an RNA made it possible to design a ribozyme that site-specifically cleaves an RNA. There are ribozymes with a size of 400 nucleotides or more as in group I intron ribozymes and M1 RNA contained in RNase P, but there are also those with an active domain of about 40 nucleotides called hammerhead or hair-pin ribozymes (Makoto Koizumi and Eiko Otsuka, Protein, Nucleic Acid and Enzyme, 1990, 35, 2191).

For example, a self-cleaving domain of a hammerhead ribozyme cleaves the 3' side of C15 of a sequence called G13U14C15. Base pair formation of U14 and A9 is considered important for the activity thereof. It is also demonstrated that cleavage can also be made at A15 or U15 instead of C15 (Koizumi, M. et al., FEBS Lett, 1988, 228, 228.) Restriction enzyme-like RNA-cleaving ribozymes that recognize the sequence UC, UU, or UA in the target RNAs can be created by designing their substrate-binding sites to be complementary to an RNA sequence near the target site (Koizumi, M. et al., FEBS Lett, 1988, 239, 285, Makoto Koizumi and Eiko Otsuka, Protein, Nucleic Acid and Enzyme, 1990, 35, 2191, Koizumi, M. et al., Nucl. Acids Res., 1989, 17, 7059.)

Further, hairpin ribozymes are also useful for the objective of the present invention. Such a ribozyme is found, for example, in the minus strand of a tobacco ringspot virus satellite RNA (Buzayan J M, Nature, 1986, 323, 349). It is demonstrated that target specific RNA-cleaving ribozymes can also be created from hairpin ribozymes (Kikuchi, Y. & Sasaki, N., Nucl. Acids Res, 1991, 19, 6751, Yo Kikuchi, Kagaku to Seibutsu [*Chemistry and Biology*], 1992, 30, 112). In this manner, expression of a gene encoding a p38 MAP kinase or the like can be inhibited by specifically cleaving a transcript of the gene by using a ribozyme.

Expression of an endogenous gene such as a p38 MAP kinase can also be suppressed by RNA interference (hereinafter, abbreviated as "RNAi") using a double-stranded RNA having a sequence that is identical or similar to a target gene sequence. RNAi is a methodology that is currently drawing attention, which can suppress the expression of a gene having a sequence that is homologous to a double strand RNA (dsRNA) when the dsRNA is incorporated directly into a cell. In mammalian cells, short stranded dsRNA (siRNA) can be used to induce RNAi. RNAi has many advantages relative to knockout mice, such as a stable effect, facilitated experiment, and low cost. SiRNA is discussed in detail in other parts of the specification.

As used herein "siRNA" is an RNA molecule having a double-stranded RNA portion consisting of 15-40 bases, where siRNA has a function of cleaving mRNA of a target gene with a sequence complementary to an antisense strand of the siRNA to suppress the expression of the target gene. Specifically, the siRNA in the present invention is an RNA comprising a double-stranded RNA portion consisting of a sense RNA strand consisting of a sequence homologous to consecutive RNA sequences in mRNA of p38 MAP kinases or the like and an antisense RNA strand consisting of a sequence complementary to the sense RNA sequence. Design and manufacture of such siRNA and mutant siRNA discussed below are within the technical competence of those skilled in the art. Any consecutive RNA regions of mRNA which is a transcript of a sequence of p38 MAP kinase or the like can be appropriately selected to make double-stranded RNA corresponding to this region, which is within the ordinary procedure performed by those skilled in the art. Further, those skilled in the art can appropriately select an siRNA sequence having a stronger RNAi effect from mRNA sequences, which are transcripts of the sequence, by a known method. Further, if one of the strands is revealed, those skilled in the art can readily find the base sequence of the other stand (complementary strand). SiRNA can be appropriately made by using a commercially available nucleic acid synthesizer. A common synthesis service can also be utilized for desired RNA synthesis.

In terms of bases, the length of a double-stranded RNA portion is 15-40 bases, preferably 15-30 bases, more preferably 15-25 bases, still more preferably 18-23 bases, and most preferably 19-21 bases. It is understood that the upper limits and the lower limits are not limited to such specific limits, and may be of any combination of the mentioned limits. The end structure of a sense strand or antisense strand of siRNA is not particularly limited, and can be appropriately selected in accordance with the objective. For example, such an end structure may have a blunt end or a sticky end (overhang). A type where the 3' end protrudes out is preferred. SiRNA having an overhang consisting of several bases, preferably 1-3 bases, and more preferably 2 bases at the 3' end of a sense RNA strand and antisense RNA strand is preferable for having a large effect of suppressing expression of a target gene in many cases. The type of bases of an overhang is not particularly limited, which may be either a base constituting an RNA or a base constituting a DNA. An example of a preferred overhang sequence includes dTdT at the 3' end (2 bp of deoxy T) and the like. Examples of preferable siRNA include, but are not limited to, all siRNA with dTdT (2 bp of deoxy T) at the 3' end of the sense or antisense strands.

Furthermore, it is also possible to use siRNA in which one to several nucleotides are deleted, substituted, inserted and/or added at one or both of the sense strand and antisense strand of the siRNA described above. One to several bases as used herein is not particularly limited, but preferably refers to 1 to 4 bases, still more preferably 1 to 3 bases, and most preferably 1 to 2 bases. Specific examples of such mutations include, but are not limited to, mutations resulting in 0 to 3 bases at the overhand portion, mutations that change the base sequence of the 3'-overhang portion to another base sequence, mutations in which the lengths of the above-described sense RNA strand and antisense RNA strand are different by 1 to 3 bases due to insertion, addition or deletion of bases, mutations substituting a base in the sense strand and/or antisense with another base, and the like. However, it is necessary that the sense strand and antisense strand can hybridize in such mutant siRNAs, and these mutant siRNAs to have the ability to suppress gene expression that is equivalent to that of siRNAs without any mutations.

SiRNA may also be a molecule with a structure in which one end is closed, such as a hairpin structure (Short Hairpin RNA; shRNA). A shRNA is an RNA comprising a sense strand RNA of a specific sequence of a target gene, an antisense strand RNA consisting of a sequence complementary to the sense strand sequence, and a linker sequence for connecting the two strands, wherein the sense strand portion hybridizes with the antisense strand portion to form a double-stranded RNA portion.

It is desirable for siRNA not to exhibit the so-called off-target effect in clinical use. An off-target effect refers to an action for suppressing the expression of another gene, besides the target gene, which is partially homologous to the siRNA used. In order to avoid an off-target effect, it is possible to confirm that a candidate siRNA does not have cross reactivity by using a DNA microarray in advance. Further, it is possible to avoid an off-target effect by confirming whether there is a gene comprising a moiety that is highly homologous to a sequence of a candidate siRNA, other than a target gene, using a known database provided by the NCBI (National Center for Biotechnology Information) or the like.

In order to make the siRNA according to the present invention, a known method, such as a method using chemical synthesis or a method using a gene recombination technique, can be appropriately used. With a method using synthesis, a double-stranded RNA can be synthesized based on sequence information by using a common method. With a method using a gene recombination technique, a siRNA can be made by constructing an expression vector encoding a sense strand sequence or an antisense strand sequence and introducing the vector into a host cell, and then obtaining each of sense strand RNA and antisense strand RNA produced by transcription. It is also possible to make a desired double-stranded RNA by expressing an shRNA forming a hairpin structure, which comprises a sense strand of a specific sequence of a target gene, an antisense strand consisting of a sequence complementary to the sense strand sequence, and a linker sequence for linking the two strands.

For a siRNA, all or part of the nucleic acid constituting the siRNA may be natural or a modified nucleic acid, as long as such a nucleic acid has activity to suppress the expression of a target gene.

The siRNA according to the present invention does not necessarily have to be a pair of double-stranded RNAs to a target sequence. It may be a mixture of a plurality of pairs (the "plurality" is not particularly limited, but preferably refers to a small number of about 2 to 5) of double-stranded RNAs to a region comprising a target sequence. In this regard, those skilled in the art can appropriately make an siRNA as a nucleic acid mixture corresponding to a target sequence by using a commercially available nucleic acid synthesizer and a DICER enzyme. A common synthesis service can also be utilized for desired RNA synthesis. It should be noted that the siRNA according to the present invention encompasses the so-called "cocktail siRNA". For the siRNA according to the present invention, not all the nucleotides have to be a ribonucleotide (RNA). In other words, in the present invention, one or plurality of ribonucleotides constituting an siRNA may be a corresponding deoxyribonucleotide. The term "corresponding" refers to having the same base type (adenine, guanine, cytosine, thymine (uracil)) but a different sugar moiety structure. For example, a deoxyribonucleotide corresponding to a ribonucleotide having adenine refers to a deoxyribonucleotide having adenine.

Furthermore, a DNA (vector) which can express the above-described RNA according to the present invention is also encompassed as a preferred embodiment of a nucleic acid which can suppress the expression of a p38 MAP kinase or the like. For example, the DNA (vector) which can express the above-described double-stranded RNA according to the present invention is a DNA having a structure in which a DNA encoding one of the strands of the double-stranded RNA and a DNA encoding the other strand of the double-stranded RNA are linked with a promoter so that each of the DNAs can be expressed. The above-described DNA according to the present invention can be appropriately made by those skilled in the art by using a common genetic engineering technique. More specifically, the expression vector according to the present invention can be made by appropriately inserting a DNA encoding the RNA of interest into various known expression vectors.

In the present invention, a modified nucleic acid may be used as a nucleic acid for suppressing the expression of a target gene. A modified nucleic acid refers to a nucleic acid, which has a modification at a nucleoside (base moiety, sugar moiety) and/or an inter-nucleoside binding site and has a structure different from that of a natural nucleic acid. Examples of "modified nucleoside" constituting a modified nucleic acid include: abasic nucleosides; arabinonucleoside, 2'-deoxyuridine, α-deoxyribonucleoside, β-L-deoxyribonucleoside, and other sugar modification bearing nucleosides; peptide nucleic acids (PNA), phosphate group-binding peptide nucleic acids (PHONA), locked nucleic acids (LNA), morpholino nucleic acids and the like. The above-described sugar modification bearing nucleosides include 2'-O-methylribose, 2'-deoxy-2'-fluororibose, 3'-O-methylribose and other substituted pentose; 1',2'-deoxyribose; arabinose; substituted arabinose sugar; and nucleoside having a sugar modification of alpha-anomer and hexose. These nucleosides may be a modified base in which the base moiety is modified. Examples of such modified bases include pyrimidine such as 5-hydroxycytosine, 5-fluorouracil, and 4-thiouracil; purine such as 6-methyladenine and 6-thioguanosine; other heterocyclic bases and the like.

Examples of a "modified inter-nucleoside bond" which constitutes a modified nucleic acid include alkyl linker, glyceryl linker, amino linker, poly(ethylene glycol) bond, inter-methyl phosphonate nucleoside bond; methylphosphonothioate, phosphotriester, phosphothiotriester, phosphorothioate, phosphorodithioate, triester prodrug, sulfone, sulfonamide, sulfamate, formacetal, N-methylhydroxylamine, carbonate, carbamate, morpholino, boranophosphonate, phosphoramidate and other bonds between non-natural nucleosides.

The nucleic acid sequence comprised in the double-stranded siRNA according to the present invention includes a siRNA for a p38 MAP kinase, other p38 MAP kinase signal members and the like.

It is also possible to introduce the nucleic acid or agent according to the present invention into a phospholipid endoplasmic reticulum such as a liposome and administer the endoplasmic reticulum. An endoplasmic reticulum in which an siRNA or shRNA is retained can be introduced into a predetermined cell using lipofection. The resulting cell is then systemically-administered, such as intravenously, intra-arterially or the like. The endoplasmic reticulum can also be locally administered to a required site in an eye or the like. While an siRNA exhibits a very good specific, post-transcription suppressing effect in vitro, the siRNA is quickly degraded in vivo due to nuclease activity in the serum. Since the duration thereof is limited, there has been a need for the development of a better and more effective delivery system. As an example, Ochiya, T et al., Nature Med., 5: 707-710, 1999, Curr. Gene Ther., 1: 31-52, 2001 reports that a biocompatible material atelocollagen, when mixed with a nucleic acid to form a complex, is a carrier which has an action of protecting a nucleic acid from a degrading enzyme in a living organism and is extremely suitable as a carrier of an siRNA. While such a form can be used, the method for introducing a nucleic acid, therapeutic or prophylactic drug according to the present invention is not limited thereto. In this manner, due to fast degradation by the action of a nucleic acid degrading enzyme in the serum in a living organism, it becomes possible to achieve continuation of the effect for an extended period of time. For example, Takeshita F. PNAS, (2003) 102 (34) 12177-82, Minakuchi Y Nucleic Acids Research (2004) 32 (13) e109 report that atelocollagen derived from bovine skin forms a complex with a nucleic acid, which has action of protecting a nucleic acid from a degrading enzyme in a living organism and is extremely suitable as a carrier of an siRNA. Such a technique can be used.

As used herein, "iFECD" (immobilized Fuchs' endothelial corneal dystrophy) is an abbreviation for immobilized cells with Fuchs' endothelial corneal dystrophy.

As used herein, "HCEC" is an abbreviation for human corneal endothelial cells. In addition, "iHCEC" is an abbreviation for immobilized human corneal endothelial cells.

As used herein, "programmed cell death" refers to a phenomenon of cells spontaneously dying at a determined time or environment as if the death is pre-programmed. Programmed cell death is used in the meaning that includes, for example, "apoptosis".

As used herein, "transforming growth factor-β (also denoted with the abbreviation TGF-β)" is used in the same meaning as those used in the art. It is a homodimer multi-functional cytokine with a molecular weight of 25 kD exhibiting a variety of biological activity, such as being responsible for pathogenesis of various sclerotic diseases, rheumatoid arthritis, and proliferative vitreoretinopathy, being deeply involved in hair loss, suppressing the functioning of immunocompetent cells while suppressing over-production of protease to prevent degradation of pulmonary tissue resulting in pulmonary emphysema, and suppressing cancer cell growth. "TGF-β signal" refers to a signal mediated by TGF-β, which is elicited by TGF-β. Examples of TGF-β signals include signals mediated by TGF-β2 in addition to signals mediated by TGF-β1, TGF-β3 or the like. In humans, TGF-β has three isoforms, TGF-β1 to β3, which have homology of about 70% and similar action. TGF-β is produced as an inactive latent form with a molecular weight of about 300 kD which is unable to bind to a receptor. The action thereof is exerted by being activated on a target cell surface or the surroundings thereof to become an active form that can bind to a receptor. Although not wishing to be bound by any theory, the action of TGF-β in a target cell is understood to be transmitted by a phosphorylation channel of a series of proteins responsible for transmitting information called Smad. First, when activated TGF-β binds to a TGF-β type II receptor on a target cell surface, a receptor complex consisting of two molecules of type II receptors and two molecules of TGF-β type I receptors is formed, and the type II receptors phosphorylate the type I receptors. It is understood that when the phosphorylated type I receptors phosphorylate Smad2 or Smad3, the phosphorylated Smad2 or Smad3 forms a complex with Smad4, which migrates to a nucleus and binds to a target sequence called CAGA box that is present in a target gene promotor region to induce transcription and expression of a target gene with a coactivator.

A transforming growth factor-β (TGF-β) signaling pathway can modulate many cellular activities, such as cell growth and differentiation, growth arrest, programmed cell death, and epithelial mesenchymal transition (EMT), by modulating the target gene. Members of the TGF-β family including TGF-β itself (e.g., TGF-β1, TGF-β2, and TGF-β3), activin, and bone morphogenetic proteins (BMP) are potent modulators of cell growth, differentiation, migration, programmed cell death, and the like.

TGF-β is a protein of about 24 kD produced by many cells including B lymphocytes, T lymphocytes, and activated macrophages and by many other cell types. Effects of TGF-β on the immune system include IL-2 receptor induction, inhibition of IL-1 induced thymocyte growth, and blocking of IFN-γ induced macrophage activation. TGF-β is considered to be involved in various pathological conditions (Border et al. (1992) J. Clin. Invest. 90:1) and is thoroughly proven to function as either a tumor suppressing substance or a tumor promotor.

Signaling of TGF-β is mediated by two serine/threonine kinase cell surface receptors TGF-βRII and ALK5. TGF-β signaling is initiated by ligand induced receptor dimerization enabling TGF-βRII to phosphorylate an ALK5 receptor. The phosphorylation activates ALK5 kinase activity, and the activated ALK5 then phosphorylates a downstream effector Smad protein (vertebrate homologue of MAD or "Mothers against DPP (decapentaplegic)" protein), Smad2 or Smad 3. A p-Smad2/3 complex with Smad4 enters a nucleus and activates transcription of a target gene.

Smad3 is a member of the R-Smad (receptor-activated Smad) subgroup of Smad and a direct mediator of transcription activation by a TGF-β receptor. A TGF-β stimulation results in phosphorylation and activation of Smad2 and Smad3, which form a complex with Smad4 ("common Smad" or "co-Smad" in vertebrates). This accumulates with the nucleus and modulates transcription of a target gene. R-Smad is localized in a cytoplasm and forms a complex with co-Smad in ligand induced phosphorylation by a TGF-β receptor, migrates to the nucleus, where it modulates gene expression associated with a cooperative transcription factor and chromatin. Smad6 and Smad7 are inhibitory Smad ("I-Smad"), i.e., they are transcriptionally induced by TGF-β and function as a TGF-β signaling inhibitor (Feng et al. (2005) Annu. Rev. Cell. Dev. Biol. 21: 659). Smad6/7 obstruct receptor-mediated activation of R-Smad to exert their inhibitory effect; and they are associated with a type I receptor, which competitively obstructs mobilization and phosphorylation of R-Smad. Smad6 and Smad7 are known to replenish E3 ubiquitin ligase, which induces ubiquitination and degradation of Smad6/7 interacting proteins.

TGF-β signaling pathways further have other pathways using BMP-7 transmission or the like, which go through ALK-1/2/3/6 via Smad1/5/8 to express a function. For TGF-β signaling pathways, see J. Massagu'e, Annu. Rev. Biochem. 1998. 67: 753-91; Vilar J M G, Jansen R, Sander C (2006) PLoS Comput Biol 2 (1):e3; Leask, A., Abraham, D. J. FASEB J. 18, 816-827 (2004); Coert Margadant & Arnoud Sonnenberg EMBO reports (2010) 11, 97-105; Joel Rosenbloom et al., Ann Intern Med. 2010; 152: 159-166 and the like.

As used herein, "corneal endothelial condition, disorder, or disease due to transforming growth factor-β (TGF-β)" refers to any corneal endothelial condition, disorder, or disease induced by TGF-β in corneal endothelial cells. In the present invention, exposure of corneal endothelial cells such as model cells of Fuchs' endothelial corneal dystrophy (e.g., iFECD) surprisingly resulted in various disorders (e.g., programmed cell death). This is a phenomenon that had not been well understood conventionally. The inventors, after further analysis of corneal endothelial condition, disorder, or disease due to a TGF-β signal, unexpectedly discovered that this disorder can be suppressed with a p38 MAPK inhibitor. A corneal endothelial condition, disorder, or disease due to a TGF-β signal is associated with a different signaling pathway of p38 MAPK, and the p38 MAPK inhibitor that was used does not suppress the signaling pathway of TGF-3. Thus, a pathway of manifestation of disease/disorder and a form of therapy and prophylaxis thereof, which were previous unresolved, were able to be discovered. Since the optimal therapeutic or prophylactic effect on corneal endothelial condition, disorder, or disease due to a TGF-β signal has been observed at a concentration that is different from the concentration of a p38 MAPK inhibitor which is generally used optimally, the present invention can be positioned as an invention providing a novel therapeutic/prophylactic technique for corneal endothelia. Examples of corneal endothelial conditions, disorders, or diseases due to a TGF-β signal include, but are not limited to, Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), and idiopathic corneal endothelial disorder and the like with observed TGF-β expression. Since the disorder discovered in the present invention or a disorder associated therewith is considered expressed or advanced especially in corneal endothelial cells or corneal endothelial tissue with higher than normal TGF-β2 expression, any corneal endothelial condition, disorder, or disease in which such corneal endothelial cells or corneal endothelial tissue are observed are especially intended as the target of the present invention.

As used herein, "corneal endothelial condition, disorder, or disease due to a mitochondrial abnormality" refers to a corneal endothelial condition, disorder, or disease due to a mitochondrial abnormality. There was hardly any progress in the analysis on mitochondrial abnormalities in a corneal endothelial condition, disorder, or disease. Mitochondrial abnormalities are considered to affect various diseases, disorders, or conditions, so that a model thereof was also provided in the present invention. For instance, when model cells of Fuchs' endothelial corneal dystrophy were exposed to TGF-β2, a significant increase in cells with a decreased mitochondrial membrane potential was surprisingly observed. After further analysis, such a decrease in mitochondrial membrane potential, surprisingly, was able to be suppressed with a p38 MAPK inhibitor. While it has been confirmed that such a decrease in mitochondrial membrane potential can be prevented by suppressing TGF-β, a p38 MAPK inhibitor has been demonstrated to not suppress the TGF-β pathway. Thus, a pathway of disease/disorder associated with a mitochondrial abnormality and a form of therapy and prophylaxis thereof, which were previous unresolved, were able to be discovered. Since the optimal therapeutic or prophylactic effect on corneal endothelial condition, disorder, or disease due to a mitochondrial abnormality has been observed at a concentration that is different from the concentration of a p38 MAPK inhibitor which is generally used optimally, the present invention can be positioned as an invention providing a novel therapeutic/prophylactic technique for corneal endothelia. Examples of corneal endothelial conditions, disorders, or diseases due to a mitochondrial abnormality include, but are not limited to, Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), and idiopathic corneal endothelial disorder with observed mitochondrial abnormality.

As used herein, "corneal endothelial condition, disorder, or disease due to endoplasmic reticulum (ER) associated stress" refers to any condition, disorder, or disease associated with endoplasmic reticulum (ER). Examples thereof include, but are not limited to, damage to corneal endothelial cells in Fuchs' endothelial corneal dystrophy, corneal endothelial disorder, decreased corneal endothelial density, guttae formation, hypertrophy of the Descemet's membrane, hypertrophy of a cornea, turbidity, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, and edema of the corneal stroma, corneal epithelial erosion, and angiogenesis, which are associated with endoplasmic reticulum (ER) associated stress.

Figure 10:
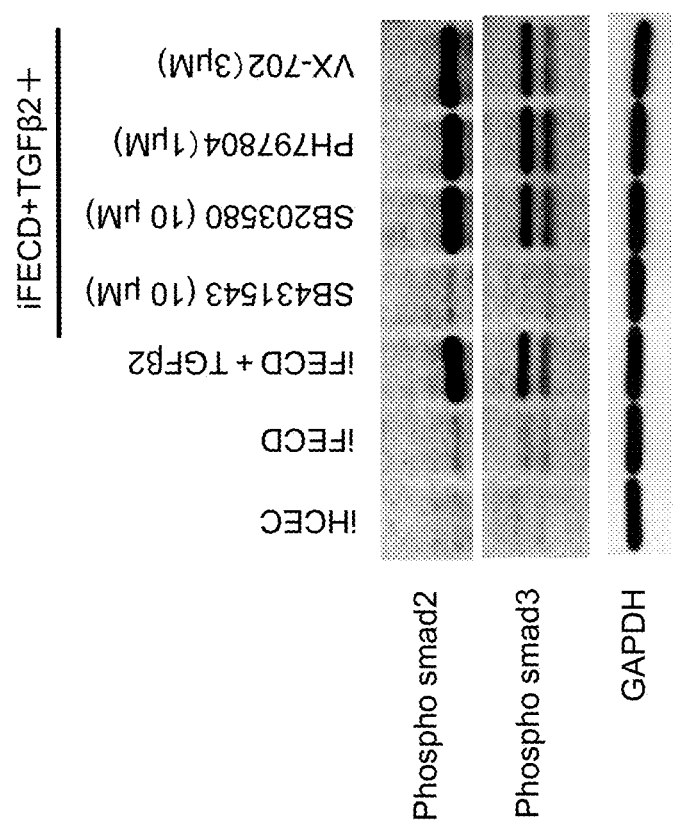
FIG. 10 shows results of western blot on smad2, smad3, and GAPDH. The picture shows, from the left lane, iHCEC, iFECD, iFECD+TGF-β2, iFECD+TGF-52+SB431543 (10 μM), iFECD+TGF-β2+SB203580 (10 μM), iFECD+TGF-β2+PH797804 (1 μM), and iFECD+TGF-β2+VX-702 (3

In a preferred embodiment, the conditions, disorders, or diseases targeted by the present invention are disorders related to Fuchs' endothelial corneal dystrophy. It is demonstrated that TGF-1 induction in corneal endothelial cells is involved in Fuchs' endothelial corneal dystrophy. It is also demonstrated that this may be involved in cell lost in FECD. Therefore, inhibition of a TGF-β signaling pathway is naturally expected to be an effective therapy for FECD. However, the inventors unexpectedly discovered that a p38 MAPK inhibitor can suppress a disorder due to a TGF-β signal. Moreover, as shown in FIG. 10, a p38 MAPK inhibitor does not obstruct the TGF-β signaling pathway, so that it can be understood that a disorder due to a TGF-β signal can be treated by a different mechanism. In this manner, the fact that a newly discovered disorder can be treated by a different mechanism is a noteworthy event in medical sciences.

Since the medicament of the present invention can treat cell damage or the like that is induced by TGF-β2, which can be one of the important causes of abnormalities or disorders in Fuchs' endothelial corneal dystrophy, the medicament is understood to be useful in treating or preventing Fuchs' endothelial corneal dystrophy. In particular, the present invention was able to suppress cell damage or programmed cell death induced by TGF-β2 in a Fuchs' endothelial corneal dystrophy model in the Examples, so that the present invention can be considered usable in therapy of patients with severe TGF-β2 associated disease in a Fuchs' endothelial corneal dystrophy model. The present invention can treat or prevent damage to corneal endothelial cells in Fuchs' endothelial corneal dystrophy, decreased corneal endothelial density, guttae formation, hypertrophy of the Descemet's membrane, hypertrophy of a cornea, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, and edema of the corneal stroma.

In the present invention, mitochondrial abnormality was demonstrated to be involved in the pathology of corneal endothelial cells with Fuchs' endothelial corneal dystrophy as demonstrated in the Examples. The present invention was discovered to be able to suppress a mitochondrial abnormality with a p38 MAP kinase inhibitor, and is understood to be useful in treating or preventing Fuchs' endothelial corneal dystrophy due to a mitochondrial abnormality. In a specific embodiment, the present invention can also suppress mitochondrial abnormalities such as a decrease in mitochondrial membrane potential, a morphological abnormality of mitochondria, a decrease in mitochondrial biosynthesis, and the like.

(General Techniques)

Molecular biological methodology, biochemical methodology, microbiological methodology used herein are well known and conventionally used in the art, which are described for example in Sambrook J. et al. (1989).

Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995).

Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Bessatsu Jikken Igaku [*Experimental Medicine, Supplemental Volume*], Idenshi Donyu Oyobi Hatsugen Kaiseki Jikken Ho [*Experimental Methods for Transgenesis & Expression Analysis*], Yodosha, 1997, or the like. The reports by Nancy Joyce et al {Joyce, 2004 #1611 and (Joyce, 2003 #7} are well known for corneal endothelial cells. However, as discussed above, long-term culture or subculture results in fibroblast-like transformation, and research for an effective culturing method are currently ongoing. Relevant portions (which may be all) thereof are incorporated herein by reference.

(Disclosure of Preferred Embodiments)

The preferred embodiments of the present invention are described hereinafter. It is understood that the embodiments are exemplification of the present invention, so that the scope of the present invention is not limited to such preferred embodiments. It should be understood that those skilled in the art can refer to the following preferred embodiments to readily make modifications within the scope of the present invention. These embodiments of the present invention can be appropriately combined with any embodiment by those skilled in the art.

<Medicament>

In one aspect, the present invention provides a medicament for use in treating or preventing a corneal endothelial condition, disorder, or disease due to a transforming growth factor-β (TGF-β) signal in corneal endothelial cells, comprising a p38 MAP kinase inhibitor.

In another aspect, the present invention provides a medicament for use in treating or preventing a corneal endothelial condition, disorder, or disease due to a mitochondrial abnormality in corneal endothelial cells, comprising a p38 MAP kinase inhibitor.

In yet another embodiment, the present invention provides a medicament for use in treating or preventing a corneal endothelial condition, disorder, or disease due to a transforming growth factor-β (TGF-β) signal and a mitochondrial abnormality in corneal endothelial cells, comprising a p38 MAP kinase inhibitor.

While a p38 MAP kinase is understood to be involved in a variety of signaling as well as inflammation, not all of the mechanism is elucidated in corneal endothelia, such that it was unexpected that a p38 MAP kinase is effective in healing or preventing a corneal endothelial disorder due to TGF-β, mitochondrial disorder, or both. Therefore, the effectiveness of a p38 MAP kinase inhibitor in treating or preventing a corneal endothelial disorder due to TGF-β, a corneal endothelial disorder due to a mitochondrial disorder, or a corneal endothelial disorder due to both was an unexpected discovery, which was only discovered by discovering that exposure of TGF-β to corneal endothelial disorder model cells of Fuchs' endothelial corneal dystrophy exacerbates the disorder or condition thereof such as an increase in programmed cell death or a mitochondrial abnormality (decrease in membrane potential) and investigating the effect of a p38 MAP kinase inhibitor using the exacerbation model.

In one embodiment, a corneal endothelial condition, disorder, or disease due to transforming growth factor-β (TGF-β) in corneal endothelial cells is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), and idiopathic corneal endothelial disorder.

In one embodiment, a corneal endothelial condition, disorder, or disease due to a mitochondrial abnormality in corneal endothelial cells is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), and idiopathic corneal endothelial disorder. In a preferred embodiment, a corneal endothelial condition, disorder, or disease due to a TGF-β signal is a corneal endothelial condition, disorder, or disease due to TGF-β2.

In one embodiment, examples of mitochondrial abnormalities include, but are not limited to, a decrease in mitochondrial membrane potential, a morphological abnormality of mitochondria, mitochondrial biosynthesis, and the like.

In yet another aspect, the present invention provides a medicament for use in treating or preventing a corneal endothelial condition, disorder, or disease due to endoplasmic reticulum (ER) associated stress in corneal endothelial cells, comprising a p38 MAP kinase inhibitor. The inventors have discovered that corneal endothelial cells are damaged by stimulating with thapsigargin, which is associated with endoplasmic reticulum (ER) associated stress, in cells of corneal endothelial disorder model of Fuchs' endothelial corneal dystrophy, to elucidate that such a disorder is suppressed with a p38 MAP kinase inhibitor. As discussed above, a p38 MAP kinase inhibitor can treat or prevent a corneal endothelial disorder or the like due to a TGF-β signal and mitochondrial abnormality, but it is surprising that a p38 MAP kinase inhibitor can also suppress endoplasmic reticulum (ER) associated stress in corneal endothelial cells. This suggests that a p38 MAP kinase inhibitor can simultaneously treat corneal endothelial disorders due to a TGF-β signal, mitochondrial abnormality and endoplasmic reticulum (ER) associated stress in corneal endothelial cells. In particular, Fuchs' endothelial corneal dystrophy is known to be associated with ER stress (Engler, C. et al. Am J Ophthalmol 149, 194-202 (2010)). For this reason, suppression of ER stress means that therapy and prophylaxis of Fuchs' endothelial corneal dystrophy can be significantly improved, and completely healed in some cases.

In one embodiment, a corneal endothelial condition, disorder, or disease due to endoplasmic reticulum (ER) associated stress in corneal endothelial cells can be caused by abnormal folding of a protein. In mammals, it is known that proteins, which have aggregated due to being unfolded, misfolding, abnormality in proteolysis, or the like (also referred to as incompletely folded protein or denatured protein (unfolded protein)), are ubiquitinated and accumulate near the centrosome by a dynein motor that moves on microtubules to form an inclusion body called aggresome. Aggresomes are generally formed by heat shock, viral infection, oxidative stress, or the like. Several diseases are known in humans that are associated with inclusion bodies in cells, such as Lewy bodies found in nerve cells in Parkinson's disease, Mallory bodies found in hepatocytes in alcoholic liver diseases, and glass-like bodies found in astrocytes in amyotrophic lateral sclerosis. The p38 MAP kinase inhibitor of the present invention can suppress endoplasmic reticulum (ER) stress due to a folding abnormality induced by thapsigargin, which is involved in the production of denatured protein. A p38 MAP kinase inhibitor also can suppress endoplasmic reticulum (ER) stress induced by TGFβ. A TGF-β inhibitor was able to suppress endoplasmic reticulum (ER) stress due to TGF-β, but not endoplasmic reticulum (ER) stress due to a folding abnormality (International Publication No. WO 2015/064768). Therefore, it was unexpected that both ER stress due to a folding abnormality and ER stress due to TGF-β can be suppressed as in the p38 MAP kinase inhibitor of the present invention.

In one embodiment, a corneal endothelial condition, disorder, or disease due to endoplasmic reticulum (ER) stress in corneal endothelial cells is selected from the group consisting of damage to corneal endothelial cells in Fuchs' endothelial corneal dystrophy, corneal endothelial disorder, decreased corneal endothelial density, and edema of the corneal stroma, corneal epithelial edema, corneal epithelial erosion, turbidity in corneal stroma, and angiogenesis resulting therefrom.

In another aspect, the present invention provides a medicament for use in treating or preventing a corneal endothelial condition, disorder, or disease due to a transforming growth factor-β (TGF-β) signal, mitochondrial abnormality, and endoplasmic reticulum (ER) associated stress in corneal endothelial cells, comprising a p38 MAP kinase inhibitor.

In one embodiment, a corneal endothelial condition, disorder, or disease due to a transforming growth factor-β (TGF-β) signal, mitochondrial abnormality, and endoplasmic reticulum (ER) associated stress in corneal endothelial cells is selected from the group consisting of damage to corneal endothelial cells in Fuchs' endothelial corneal dystrophy, corneal endothelial disorder, decreased corneal endothelial density, and edema of the corneal stroma, corneal epithelial edema, corneal epithelial erosion, turbidity in corneal stroma, and angiogenesis resulting therefrom.

In one embodiment, a corneal endothelial condition, disorder, or disease due to a transforming growth factor-3 (TGF-β) signal, mitochondrial abnormality, and endoplasmic reticulum (ER) associated stress in corneal endothelial cells comprises Fuchs' endothelial corneal dystrophy.

In one embodiment, examples of utilization methods of the present invention include, but are not limited to, eye drops, as well as administration methods such as injection into the anterior chamber, impregnation into a controlled-release agent, subconjunctival injection, and systemic administration (oral administration and intravenous injection).

In one embodiment, the p38 MAP kinase inhibitor used in the present invention comprises at least one selected from the group consisting of 4-(4-fluorophenyl)-2-(4-hydroxyphenyl)-5-(4-pyridyl)-1H-imidazole (SB-202190), trans-4-[4-(4-fluorophenyl)-5-(2-methoxy-4-pyrimidinyl)-1H-imidazole-1-yl]cyclohexanol (SB-239063), 4-(4-fluorophenyl)-2-(4-methylsulfinylphenyl)-5-(4-pyridyl)-1H-i midazole (SB-203580), 4-(4-fluorophenyl)-5-(2-methoxypyrimidine-4-yl)-1-(piperidine-4-yl)imidazole (SB-242235), 4-(4-fluorophenyl)-2-(4-hydroxy-1-butynyl)-1-(3-phenylpropyl)-5-(4-pyridyl)imidazole (RWJ-67657), 4-(4-fluorophenyl)-1-(piperidine-4-yl)-5-(4-pyridyl)imidazole (HEP-689), (S)-2-(2-amino-3-phenylpropylamino)-1-methyl-5-(2-naphthyl)-4-(4-pyridyl)pyrimidine-6-one (AMG-548), 2-chloro-4-(4-fluoro-2-methylanilino)-2'-methylbenzophenone (EO-1606), 3-(4-chlorophenyl)-5-(1-hydroxyacetylpiperidine-4-yl)-4-(pyrimidine-4-yl)pyrazole (SD-06), 5-(2,6-dichlorophenyl)-2-(2,4-difluorophenylthio)pyrimido[3,4-b]pyridazine-6-one (VX-745), 4-acetylamino-N-tert-butylbenzamide (CPI-1189), N-[3-tert-butyl-1-(4-methylphenyl)pyrazole-5-yl)-N'-[4-(2-morpholinoethoxy)-1-naphthyl]urea (Doramapimod), 2-benzamide-4-[2-ethyl-4-(3-methylphenyl)thiazole-5-yl]pyridine (TAK-715), Talmapimod (SCIO-469), 1-(carbamoyl-6-(2,4-difluorophenyl)pyridine-2-yl)-1-(2,6-difluorophenyl)urea (VX-702); 2-(2,4-difluorophenyl)-6-(1-(2,6-difluorophenyl)ureido) nicotinamide), dilmapimod (GSK-681323), 4-(5-(cyclopropylcarbamoyl)-2-methylphenylamino)-5-methyl-N-propylpyrrolo(1,2-f)(1,2,4)triazine-6-carboxamide (PS-540446), anti-FGF-7 antibody (SC-80036), AVE-9940 (Sanofi-Aventis), [5-amino-1-(4-fluorophenyl)-1H-pyrazole-4-yl][3-(3-amino-2-hydroxypropoxy)phenyl]methanone (RO-320-1195), 1-(1,3-dihydroxyprop-2-yl)-4-(4-fluorophenyl)-5-[2-phenoxypyrimidine-4-yl]imidazole (SB-281832), 2-[5-({4-[(4-fluorophenyl)methyl]piperidine-1-yl}carbonyl)-6-methoxy-1-methyl-1H-indole-3-yl]-N,N'-dimethyl-2-oxoacetamide (SCIO-323), 2-(5-tert-butyl-2-m-tolyl-2H-pyrazole-3-yl)-2-hydroxyimide-N-[4-(2-morpholine-4-yl-ethoxy)-naphthalene-1-yl]-acetamide (KC-706), N,N'-bis[3,5-bis[1-(2-amidinohydrazono)ethyl]phenyl]decandiamide, N,N'-bis[3,5-bis[1-[2-(aminoiminomethyl)hydrazono]ethyl] phenyl]decandiamide (Semapimod), 3-(3-bromo-4-((2,4-difluorobenzyl)oxy)-6-methyl-2-oxopyridine-1(2H)-yl)-N,4-dimethylbenzamide (PH-797804), and 5-(2-(tert-butyl)-5-(4-fluorophenyl)-1H-imidazole-4-yl)-3-neopentyl-3H-imidazo[4,5-b]pyridine-2-amine (LY2228820).

The above p38 MAPK inhibitors may be used alone or in combination in the medicament of the present invention. The concentration of a p38 MAP kinase agent used in the present invention is generally about 0.1-100 µM (µmol/L), preferably about 0.1-30 µM, and more preferably about 1-10 µM. When two or more types of p38 MAPK inhibitors are used in combination, the concentration can be appropriately changed. Examples of other concentration ranges include, but are not limited to, generally about 0.001-100 µM, preferably about 0.01-75 µM, about 0.05-50 µM, about 1-10 µM, about 0.01-10 µM, about 0.05-10 µM, about 0.075-10 µM, about 0.1-10 µM, about 0.5-10 µM, about 0.75-10 µM, about 1.0-10 µM, about 1.25-10 µM, about 1.5-10 µM, about 1.75-10 µM, about 2.0-10 µM, about 2.5-10 µM, about 3.0-10 µM, about 4.0-10 µM, about 5.0-10 µM, about 6.0-10 µM, about 7.0-10 µM, about 8.0-10 µM, about 9.0-10 µM, about 0.01-50 µM, about 0.05-5.0 µM, about 0.075-5.0 µM, about 0.1-5.0 µM, about 0.5-5.0 µM, about 0.75-5.0 µM, about 1.0-5.0 µM, about 1.25-5.0 µM, about 1.5-5.0 µM, about 1.75-5.0 µM, about 2.0-5.0 µM, about 2.5-5.0 µM, about 3.0-5.0 µM, about 4.0-5.0 µM, about 0.01-3.0 µM, about 0.05-3.0 µM, about 0.075-3.0 µM, about 0.1-3.0 µM, about 0.5-3.0 µM, about 0.75-3.0 µM, about 1.0-3.0 µM, about 1.25-3.0 µM, about 1.5-3.0 µM, about 1.75-3.0 µM, about 2.0-3.0 µM, about 0.01-1.0 µM, about 0.05-1.0 µM, about 0.075-1.0 µM, about 0.1-1.0 µM, about 0.5-1.0 µM, about 0.75-1.0 µM, about 0.09-35 µM, about 0.09-3.2 µM, and more preferably about 0.05-1.0 µM, about 0.075-1.0 µM, about 0.1-1.0 µM, about 0.5-1.0 µM, and about 0.75-1.0 µM.

In a preferred embodiment, a p38 MAP kinase inhibitor is selected from, for example, the group consisting of 4-(4-fluorophenyl)-2-(4-methylsulfinylphenyl)-5-(4-pyridyl)-1H-imidazole (SB203580), 1-(carbamoyl-6-(2,4-difluorophenyl)pyridin-2-yl)-1-(2,6-difluorophenyl)urea (VX-702), 3-[3-bromo-4-[(2,4-difluorophenyl)methoxy)-6-methyl-2-oxopyridin-1-yl]-N,4-dimethylbenzamide (PH797804), and salts thereof.

In another embodiment, a p38 MAP kinase inhibitor is 4-(4-fluorophenyl)-2-(4-methylsulfinylphenyl)-5-(4-pyridyl)-1H-imidazole (SB203580). The concentration of SB203580 used is generally about 3 µM to about 30 µM, preferably about 5 to about 15 µM, and more preferably about 10 µM.

In another embodiment, a p38 MAP kinase inhibitor is 1-(carbamoyl-6-(2,4-difluorophenyl)pyridin-2-yl)-1-(2,6-difluorophenyl)urea (VX-702). The concentration of VX-702 used is generally about 1 µM to about 10 µM, preferably about 1.5 µM to about 6 µM, and more preferably about 3 µM.

In yet another embodiment, a p38 MAP kinase inhibitor is 3-[3-bromo-4-[(2,4-difluorophenyl)methoxy]-6-methyl-2-oxopyridin-1-yl]-N,4-dimethylbenzamide (PH797804). The concentration of PH797804 used is generally about 0.3 µM to about 3 µM, preferably about 0.5 µM to about 2 µM, and more preferably about 1 µM.

While the concentration at which the aforementioned p38 MAP kinase inhibitors (e.g., SB203580, VX-702, and PH-797804) exert their normal potency as a p38 MAP kinase inhibitor is considered sub-µM, it was elucidated that an effect of suppressing a corneal endothelial disorder is exerted at an unexpectedly higher concentration (order of µM) in a system using model cells of Fuchs' endothelial corneal dystrophy.

Although not wishing to be bound by any theory, conventional wisdom could not have expected that a conventional p38 MAP kinase inhibitor can treat or prevent a corneal endothelial condition, disorder, or disease due to at least one of transforming growth factor-β (TGF-β) and mitochondrial abnormality. It was also elucidated that the optimal concentration of each of the aforementioned p38 MAP kinase inhibitors differs from the concentration as a conventionally known p38 MAP kinase inhibitor. A p38 MAP kinase inhibitor also achieves, with respect to the above, therapy or prophylaxis of a corneal endothelial condition, disorder, or disease due to at least one of transforming growth factor-β (TGF-β) and mitochondrial abnormality, which was previously unknown, thus providing a therapeutic or prophylactic agent that is different from previously expected agents.

In one embodiment, a therapeutic or prophylactic medicament of the present invention can be targeted for any animal with a corneal endothelium, such as mammals. Such a medicament is preferably intended for treating or preventing a primate corneal endothelium. The subject of therapy or prophylaxis is preferably a human corneal endothelium.

In another aspect, the present invention provides a method of treating or preventing a corneal endothelial condition, disorder, or disease due to at least one of transforming growth factor-β (TGF-β) and mitochondrial abnormality in corneal endothelial cells, comprising administering an effective dose of a p38 MAP kinase inhibitor to a subject in need thereof.

As used herein, a "subject" refers to a target of administration (transplant) of a therapeutic or prophylactic medicament or method of the present invention. Examples of subjects include mammals (e.g., human, mouse, rat, hamster, rabbit, cat, dog, cow, horse, sheep, monkey and the like), but primates are preferable and humans are especially preferable.

The effective dose of the medicament of the present invention, which is effective in treating a specific disease, disorder, or condition, can vary depending on the properties of a disorder or condition, but this can be determined by those skilled in the art with standard clinical techniques based on the descriptions in the present specification. It is also possible to use an in vitro assay to assist in identifying the optimal range of dosage as needed. Since an accurate dose to be used in a formulation can vary depending on the route of administration and the severity of a disease or disorder, the dose should be determined in accordance with the judgment of a physician or the condition of each patient. However, the dosage, while not particularly limited, may be, for example, 0.001, 1, 5, 10, 15, 100, or 1000 mg/kg body weight or a value between two such values. The interval of administration, while not particularly limited, may be for example one or two doses for every 1, 7, 14, 21, or 28 days, or one or two doses for every number of days between two such values. The dosage, number of doses, administration interval, and administration method may be appropriately selected depending on the age or body weight of a patient, condition, dosage form, target organ, or the like. For example, the present invention can be used as an eye drop. The medicament of the present invention can also be injected into the anterior chamber. A therapeutic drug preferably comprises a therapeutically effective dose or an effective dose of active ingredients at which a desired action is exerted. It may be determined that there is a therapeutic effect when a therapeutic marker significantly decreases after administration. The effective dose can be estimated from a dose-response curve obtained from an in vitro or animal model testing system.

<Composition for Preservation>

In another aspect, the present invention provides a composition for preservation of corneal endothelial cells, comprising a p38 MAP kinase inhibitor. In a preferred embodiment, preservation is cryopreservation. It is understood that the p38 MAP kinase inhibitor used in the present invention can have any form explained herein such as an embodiment that is suitable as a composition for preservation among embodiments explained as a medicament. As used herein, a "composition for preservation" is a composition for preserving a corneal fragment extracted from a donor until the fragment is transplanted into a recipient, or for preserving corneal endothelial cells before being grown or after being grown.

In one embodiment, the composition for preservation of the present invention can be prepared by adding a p38 MAP kinase inhibitor of the present invention to a conventionally used preservative or preservation solution. Examples of such a cornea preservation solution include preservation solutions that are commonly used for corneal transplant (sclerocornea fragment preservation solution (Optisol GS®) or eye ball preservation solution for corneal transplant (EPII®)), saline, phosphate-buffered saline (PBS) and the like.

The composition for preservation of the present invention is used for preserving a cornea that is used in organ transplant or the like. The composition for preservation of the present invention is also used as a preservation solution for cryopreserving corneal endothelial cells or as a component thereof.

In another embodiment of the composition for preservation of the present invention used for cryopreservation, an existing cryopreservation solution can be used by adding a composition for preservation comprising a caspase inhibitor of the present invention. Examples of a cryopreservation solution include, but are not limited to, CELLBANKER® series provided by Takara Bio (CELL BANKER PLUS (catalog number: CB021), CELL BANKER 2 (catalog number: CB031), STEM-CELLBANKER (catalog number: CB043) and the like), KM BANKER (Kohjin Bio catalog number: KOJ-16092005), and Freezing Medium, Animal Component Free, CRYO Defined (also denoted as Cnt-CRYO) (CELLNTEC catalog number: CnT-CRYO-50). In yet another embodiment, the cryopreservation solution used may be KM BANKER. It is understood that those skilled in the art can use a suitable modified cryopreservation solution by appropriately changing a constituent component of the aforementioned cryopreservation solution or by adding an additional constituent component. Glycerol, dimethyl sulfoxide, propylene glycol, acetamide, or the like may be further added to the preservation solution of the present invention for cryopreservation.

Reference literatures such as scientific literatures, patents, and patent applications cited herein are incorporated herein by reference to the same extent that the entirety of each document is specifically described.

The present invention has been explained while showing preferred embodiments to facilitate understanding. The present invention is explained hereinafter based on Examples. The above explanation and the following Examples are not provided to limit the present invention, but for the sole purpose of exemplification. Thus, the scope of the present invention is not limited to the embodiments and Examples that are specifically disclosed herein and is limited only by the scope of claims.

EXAMPLES

Hereinafter, examples of the present invention are described. Biological samples or the like, where applicable, were handled in compliance with the standards enacted by the Ministry of Health, Labour and Welfare, Ministry of Education, Culture, Sports, Science and Technology, or the like and, where applicable, based on the Helsinki Declaration or ethical codes prepared based thereon. For the donation of eyes used for the study, consent was obtained from close relatives of all deceased donors. The present study was approved by the ethics committee or a corresponding body of the University of Erlangen-Nuremberg (Germany) and SightLife™ (Seattle, Wash.) eye bank.

Preparation Example: Production of Fuchs' Endothelial Corneal Dystrophy Patient Derived Immobilized Corneal Endothelial Cell Line (iFECD) Mode In the present example, an immobilized corneal endothelial cell line (iFECD) was made from corneal endothelial cells from Fuchs' endothelial corneal dystrophy patients.

(Culture Method)

Corneal endothelial cells were mechanically peeled off with a basal membrane from a cornea for research, purchased from the Seattle Eye Bank. After collagenase was used to detach and collect the corneal endothelial cell from the basal membrane, the cells were subjected to primary culture. For a medium, Opti-MEM I Reduced-Serum Medium, Liquid (INVITROGEN catalog No.: 31985-070), to which 8% FBS (BIOWEST, catalog No.: S1820-500), 200 mg/ml of $CaCl_2*2H_2O$ (SIGMA catalog No.: C7902-500G), 0.08% of chondroitin sulfate (SIGMA catalog No.: C9819-5G), 20 µg/ml of ascorbic acid (SIGMA catalog No.: A4544-25G), 50 µg/ml of gentamicin (INVITROGEN catalog No.: 15710-064) and 5 ng/ml of EGF (INVITROGEN catalog No.: PHG0311) were added, and acclimated for a 3T3 feeder cell was used as a basal medium. Further, the cells were cultured in a basal medium to which SB431542 (1 µmol/L) and SB203580 (4-(4-fluorophenyl)-2-(4-methylsulfonylphenyl)-5(4-pyridyl) imidazole<4-[4-(4-fluorphenyl)-2-(4-methylsulfinylphenyl)-1H-imidazole-5-yl]pyridine) (1 µmol/L) were added (also referred to as "SB203580+SB431542+3T3 acclimated medium" herein).

(Method of Acquisition)

Corneal endothelial cells were obtained with approval from an ethics committee and written consent from 3 human patients who suffered from bullous keratopathy according to a clinical diagnosis of Fuchs' endothelial corneal dystrophy and underwent corneal endothelial transplant (Descemet's Membrane Endothelial Keratoplasty=DMEK). For DMEK, pathological corneal endothelial cells were mechanically peeled off with the basal membrane, i.e., the Descemet's membrane, and immersed in a cornea preservation solution Optisol-GS (Bauch & Lomb). Collagenase treatment was then applied to enzymatically collect the corneal endothelial cells, and the cells were cultured with a SB203580+SB431542+3T3 acclimated medium. For cultured corneal endothelial cells from a Fuchs' endothelial corneal dystrophy patient, SV40 large T antigen and hTERT gene were amplified by PCR and introduced into a lentiviral vector (pLenti6.3_V5-TOPO; Life Technologies Inc). The lentiviral vector was then used to infect 293T cells (RCB2202; Riken Bioresource Center, Ibaraki, Japan) with a transfection reagent (Fugene H D; Promega Corp., Madison, Wis.) and three types of helper plasmids (pLP1, pLP2, pLP/VSVG; Life Technologies Inc.). Culture supernatant comprising viruses was collected after 48 hours from the infection, 5 µg/ml of polybrene was used and added to a culture solution of cultured corneal endothelial cells from a Fuchs' endothelial corneal dystrophy patient, and SV40 large T antigen and hTERT gene were introduced. Images of immobilized corneal endothelial cell line (iFECD) from Fuchs' endothelial corneal dystrophy patients from a phase difference microscope were studied. Corneal endothelial cells cultured from a research cornea imported from the Seattle Eye Bank were immobilized by the same method to make an immobilized cell line of normal corneal endothelial cells (iHCEC) as a control. When images of the immobilized corneal endothelial cell line (iFECD) and the immobilized corneal endothelial cell line from a healthy donor (iHCEC) from a phase difference microscope are studied, both iHCEC and iFECD have a layer of polygonal form as in normal corneal endothelial cells. IHCEC and iFECD were maintained and cultured with DMEM+10% FBS.

(Reagent)

In the following Examples, SB203580, PH-797804, and VX-702 were used as p38 MAPK inhibitors. A TGF-1 inhibitor SB431542 was also used as a comparative example. Unless specifically noted otherwise, the concentrations of the p38 MAPK inhibitors and the TGF-β inhibitor used are the following. DMSO (Dimethyl Sulfoxide Sterile-filtered) (Nacalai Tesque, 13408-64) was used as a solvent.

SB431542 10 µM (WAKO, catalog number: 192-16541)
SB203580 10 µM (Cayman, catalog number: 13067)
PH-797804 1 µM (Selleck Chemicals, catalog number: S2726) VX-702 3 µM (Selleck Chemicals, catalog number: S6005)

Example 1: Suppression of Cell Damage and Programmed Cell Death in a Corneal Endothelial Disorder Model of Fuchs' Endothelial Corneal Dystrophy This Example studied the suppression of cell damage and programmed cell death due to a p38 MAPK inhibitor in a corneal endothelial disorder model of Fuchs' endothelial corneal dystrophy.

(Materials and Methods)

The following reagents were used.
Accutaze (200 l/sample)
1× Binding Buffer (92.5 µl/sample)
Annexin (5 µl/sample)
PI (2.5 µl/sample)

Figure 1:
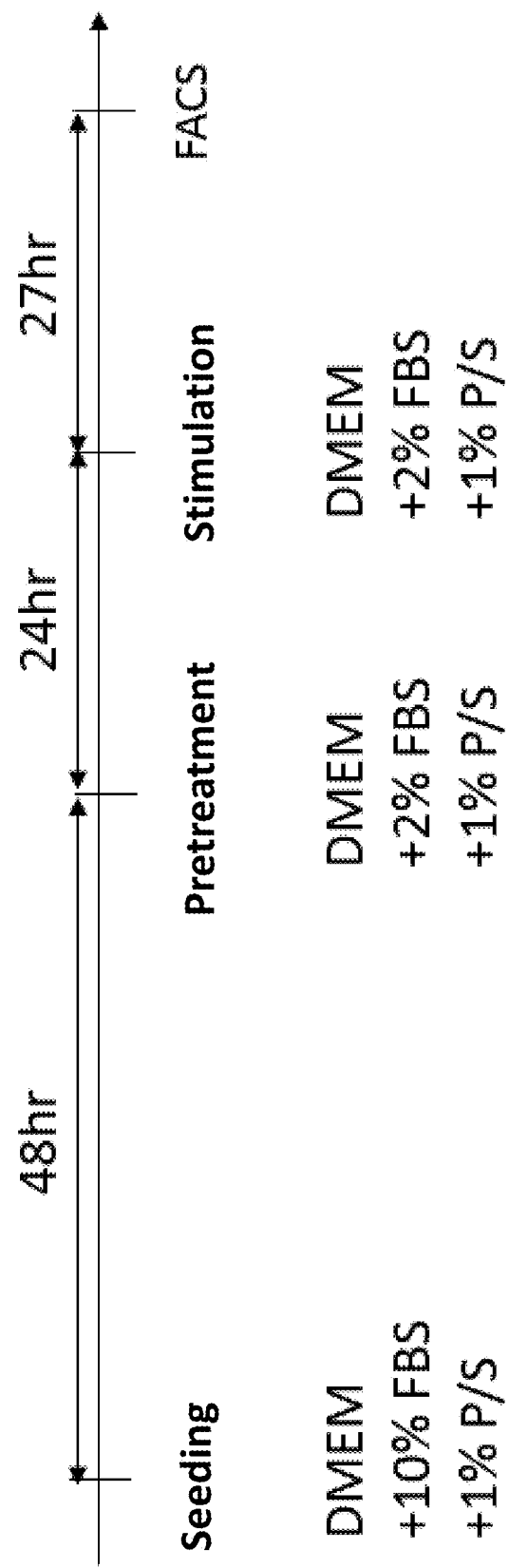
FIG. 1 shows a summary of the protocol of Example 1.

FIG. 1 shows a summary of the protocol of this Example.

The medium was removed from a culture dish in which immobilized human corneal endothelial cells were being cultured, and the cells were supplemented with 1×PBS (−) that was preheated to 37° C., and were washed. This was repeated twice. The cells were supplemented again with 1×PBS (−) and incubated for 5 minutes at 37° C. (5% $CO_2$). After removing the PBS (−), the cells were supplemented with 0.05% Trypsin-EDTA (Nacalai Tesque, 35554-64) and incubated for 5 minutes at 37° C. (5% $CO_2$). The cells were then suspended in a medium, and collected by centrifugation at 1500 rpm for 3 minutes. DMEM (Nacalai Tesque, 08456-94)+10% FBS (Biowest, S1820-500)+1% P/S (penicillin-streptomycin mixture) (Nacalai Tesque, 26252-94) was used as the medium.

Immobilized human corneal endothelial cells (lot: iFECD3-5) were seeded on a 12-well plate at a ratio of $8×10^4$ cells per well and cultured for 48 hours at 37° C. (5% $CO_2$). DMEM+10% FBS+1% P/S was used as the medium.

After 48 hours, the medium was removed. Each inhibitor was added to culture the cells for 24 hours. DMSO (Dimethyl Sulfoxide Sterile-filtered) (Nacalai Tesque, 13408-64) was added to the control group and the TGF-52 group. DMEM+2% FBS+1% P/S was used as the medium.

After 24 hours, the medium was removed. A medium containing 10 ng/ml of Recombinant Human TGF-β2 (R&D systems, RND302-B2-002) and each inhibitor was added to culture the cells for 27 hours. DMSO was added to the control group. DMEM+2% FBS+1% P/S was used as the medium. After 27 hours, the cell morphology and programmed cell death were observed under a phase differential microscope.

After observation, flow cytometry was performed by the following procedure with Annexin V as an indicator.

1) Sample Preparation

The medium in the wells was removed, and the cells were washed twice with 1×PBS (−). Accutase (AT104 INNOVAT) was added to incubate the cells for 5 minutes at 37° C. (5% $CO_2$). The inside of the wells was then washed once with the medium. 800 g was centrifuged at 4° C. for 5 minutes. The supernatant was discarded. 1×PBS (−) was subsequently added and pipetted into a tube, and then 800 g was again centrifuged at 4° C. for 5 minutes. The supernatant was discarded to obtain precipitates. 1× Binding Buffer was then added. Annexin V and PI were stained using MEBCYTO- Apoptosis kit (Annexin V-FITC kit) (MBL) (Lot. 027FA). DMEM+2% FBS+1% P/S was used as the medium.

2) Flow Cytometry

The sample collected above was analyzed using BD Accuri C6 Flow Cytometer (BD).

(Results)

(P38 MAPK Inhibitor Suppresses Cell Damage in Corneal Endothelial Disorder Model of Fuchs' Endothelial Corneal Dystrophy)

Figure 2:
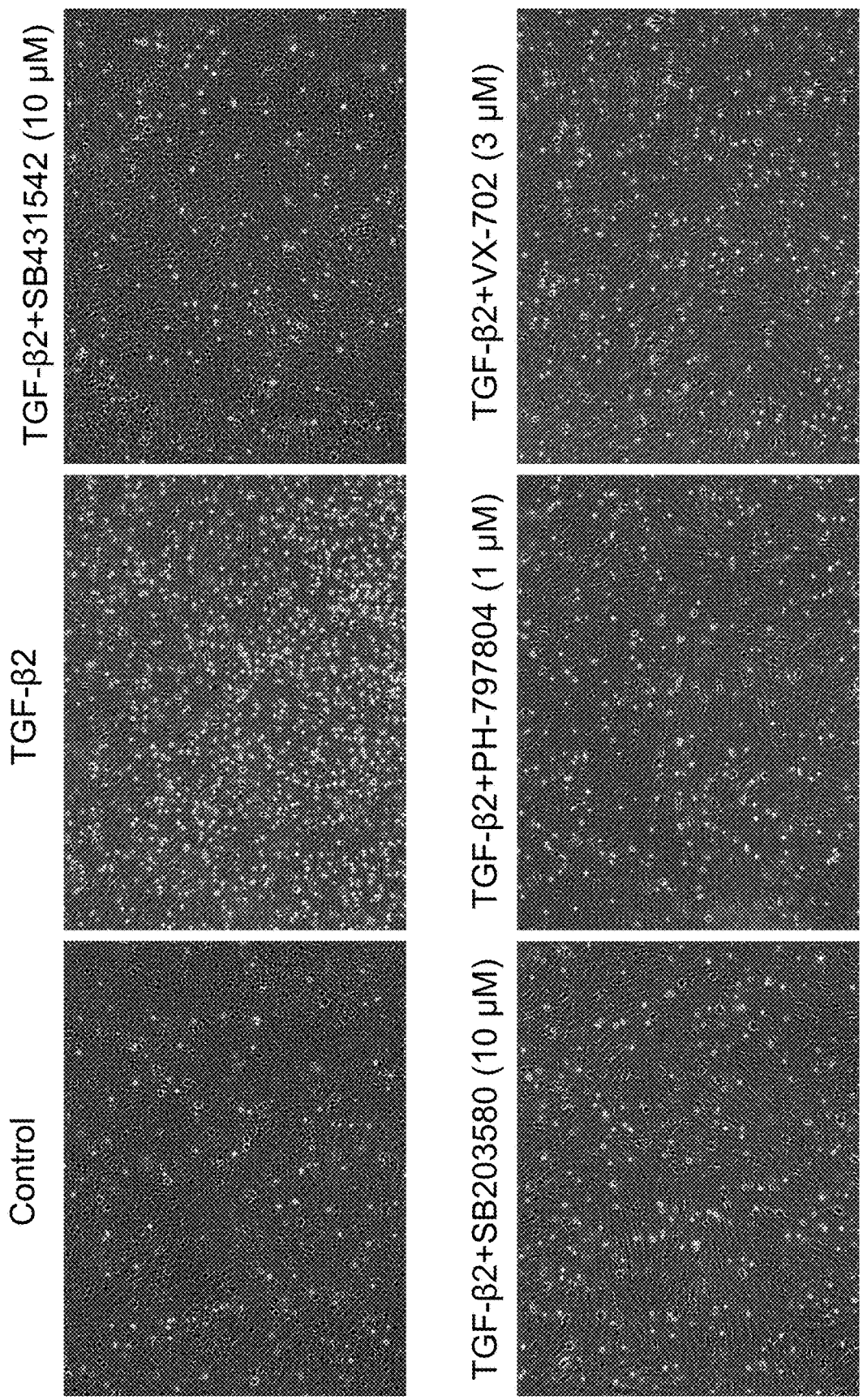
FIG. 2 shows pictures from a phase differential microscope of immobilized human corneal endothelial cells after 27 hours from stimulating immobilized human corneal endothelial cells, which were pretreated with each p38 MAP kinase inhibitor, with TGF-β2. (Top panel shows, from the left, control, TGF-β2, and TGF-β2+SB431542 (10 μM). The bottom panel shows, from the left, TGF-β2+SB203580 (10 μM), TGF-β2+PH-797804 (1 μM), and TGF-β2+VX-702 (3 μM). A p38 MAPK inhibitor suppresses cell damage due to a TGF-β signal in a corneal endothelial disorder model of Fuchs' endothelial corneal dystrophy.

FIG. 2 shows the results. When immobilized human corneal endothelial cells were stimulated with TGF-β2 in the absence of p38 MAPK, cells were found to be significantly damaged. On the other hand, it was observed that damage to corneal endothelial cells was suppressed when pretreated with a p38 MAPK inhibitor, in the same manner as when pretreated with a TGF-β2 inhibitor SB431542. Therefore, a p38 MAPK inhibitor can suppress cell damage due to TGF-β2 stimulation.

(P38 MAPK Inhibitor Suppresses Programmed Cell Death in Corneal Endothelial Disorder Model of Fuchs' Endothelial Corneal Dystrophy)

Figure 3:
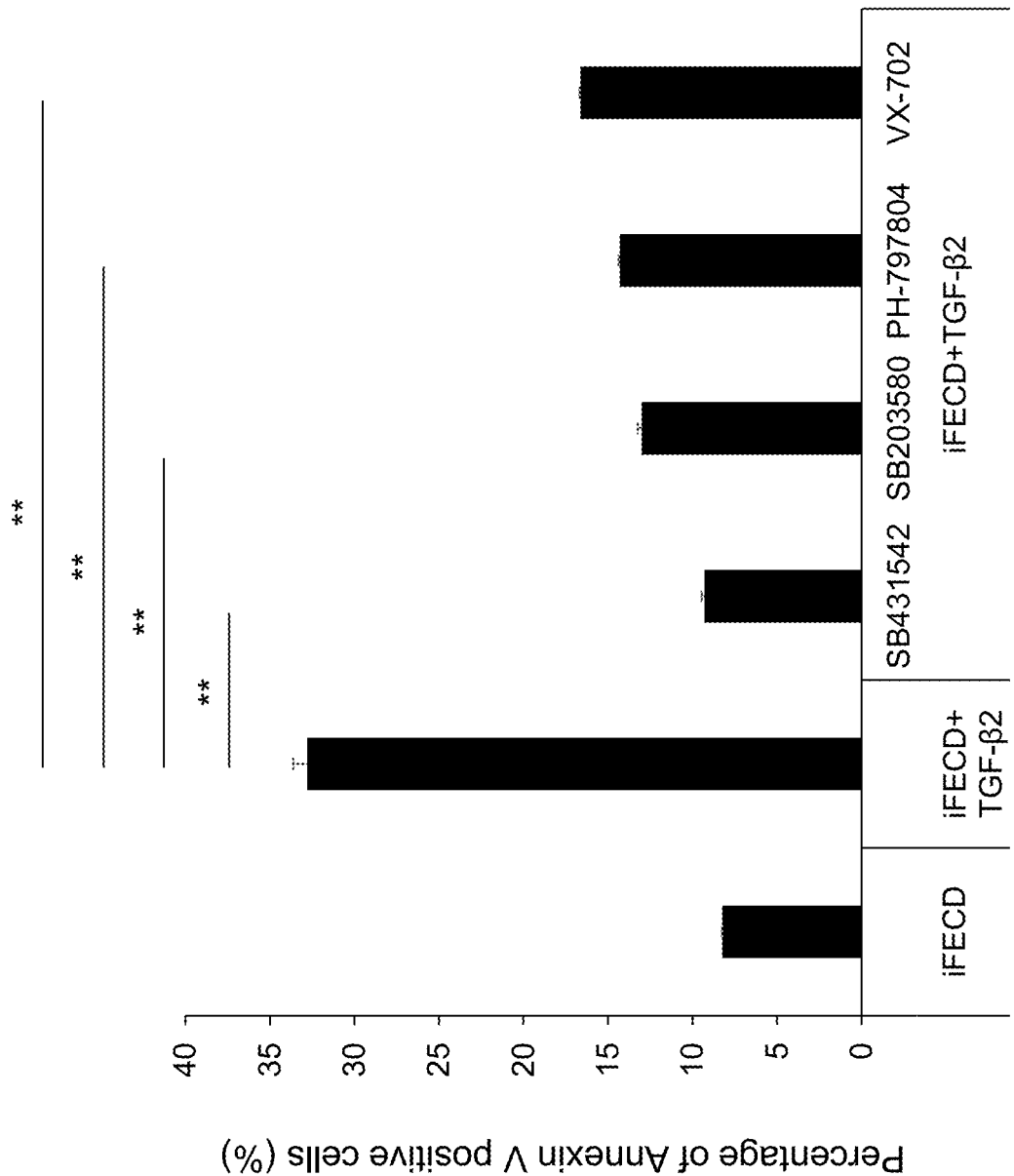
FIG. 3 shows the percentage of Annexin V positive cells (%) measured by flow cytometry. The graph shows, from the left, iFECD, iFECD+TGF-β2, iFECD+TGF-β2+SB431542, iFECD+TGF-β2+SB203580, iFECD+TGF-β2+PH-797804, and iFECD+TGF-β2+VX-702. The data is shown as mean±SEM and n=3. The p value was calculated using Dunnett's test. ** indicates statistical significance (p<0.01). As shown, a p38 MAPK inhibitor suppresses programmed cell death in a corneal endothelial disorder model of Fuchs' endothelial corneal dystrophy.

As shown in FIG. 3, the p38 MAPK inhibitor-added group was confirmed to have a significantly reduced percentage of Annexin V-positive apoptotic cells compared to the TGF-β2 group.

Example 2: Observation of Mitochondrial Membrane Potential by Confocal Microscope This Example studied the suppression of a decrease in mitochondrial membrane potential by a p38 MAPK inhibitor in a corneal endothelial disorder model of Fuchs' endothelial corneal dystrophy using a confocal microscope.

(Materials and Methods)

Figure 4:
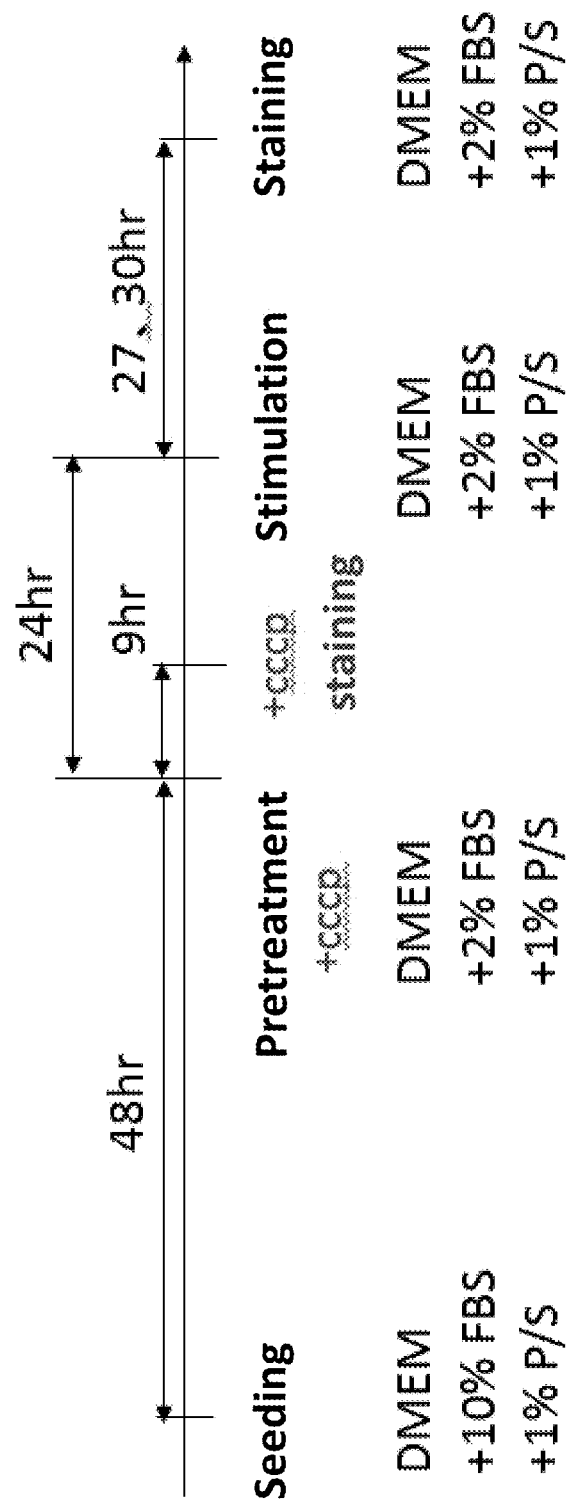
FIG. 4 shows a summary of the protocol of Example 2.

FIG. 4 shows a summary of the protocol of this Example.

The medium was removed from a culture dish in which immobilized human corneal endothelial cells were being cultured, and the cells were supplemented with 1×PBS (−) that was preheated to 37° C., and were washed. This was repeated twice. The cells were supplemented again with 1×PBS (−) and incubated for 5 minutes at 37° C. (5% $CO_2$). After removing the PBS (−), the cells were supplemented with 0.05% Trypsin-EDTA (Nacalai Tesque, 35554-64) and incubated for 5 minutes at 37° C. (5% $CO_2$). The cells were then suspended in a medium, and collected by centrifugation at 1500 rpm for 3 minutes. DMEM (Nacalai Tesque, 08456-94)+10% FBS (Biowest, S1820-500)+1% P/S (Nacalai Tesque, 26252-94) was used as the medium.

Immobilized human corneal endothelial cells (lot: iFECD3-5) were seeded on a 48-well plate at a ratio of $4 \times 10^4$ cells per well and cultured for 48 hours at 37° C. (5% $CO_2$). DMEM+10% FBS+1% P/S was used as the medium.

After 48 hours, the medium was removed. Each inhibitor was added to culture the cells for 24 hours (pretreatment). DMSO (Dimethyl Sulfoxide Sterile-filtered) (Nacalai Tesque, 13408-64) was added to the control group and the TGF-β2 group. The CCCP group was supplemented with CCCP (abcam, ab141229), so that the final concentration was 50 μmol/L, and cultured for 9 hours. Samples were prepared by the following procedure after 9 hours for the CCCP group and after 24 hours for other samples. DMEM+2% FBS+1% P/S was used as the medium.

After 24 hours from pretreatment, the medium was removed. A medium containing 10 ng/ml of Recombinant Human TGF-β2 (R&D systems, RND302-B2-002) and each inhibitor was added to culture the cells for 30 hours. DMSO was added to the control group. DMEM+2% FBS+1% P/S was used as the medium.

Mitochondrial membrane potential was analyzed by the following procedure with a JC-1 stain.

1) Sample Preparation

The medium in the wells was removed, and the cells were washed twice with a medium. A mixture of 250 μl of medium and 2.5 μl of MitoScreen (JC-1) (BD Biosciences, 551302) was added to incubate the cells at 37° C. (5% $CO_2$) for 15 minutes. The medium in the wells was removed. The cells were immersed in 4% PFA for 10 minutes for immobilization. The cells were then washed twice with 1×PBS (−) and supplemented with DAPI (1000× dilution) to stain the nucleus for 30 minutes. The cells were washed twice again with 1×PBS (−) and supplemented with an antifade agent for mounting.

2) Observation of Fluorescence

The JC-1 and the nucleus were observed under a confocal microscope for the sample produced above.

(Results)

(P38 MAPK Inhibitor Suppresses Decrease in Mitochondrial Membrane Potential in Corneal Endothelial Disorder Model of Fuchs' Endothelial Corneal Dystrophy)

Figure 5:
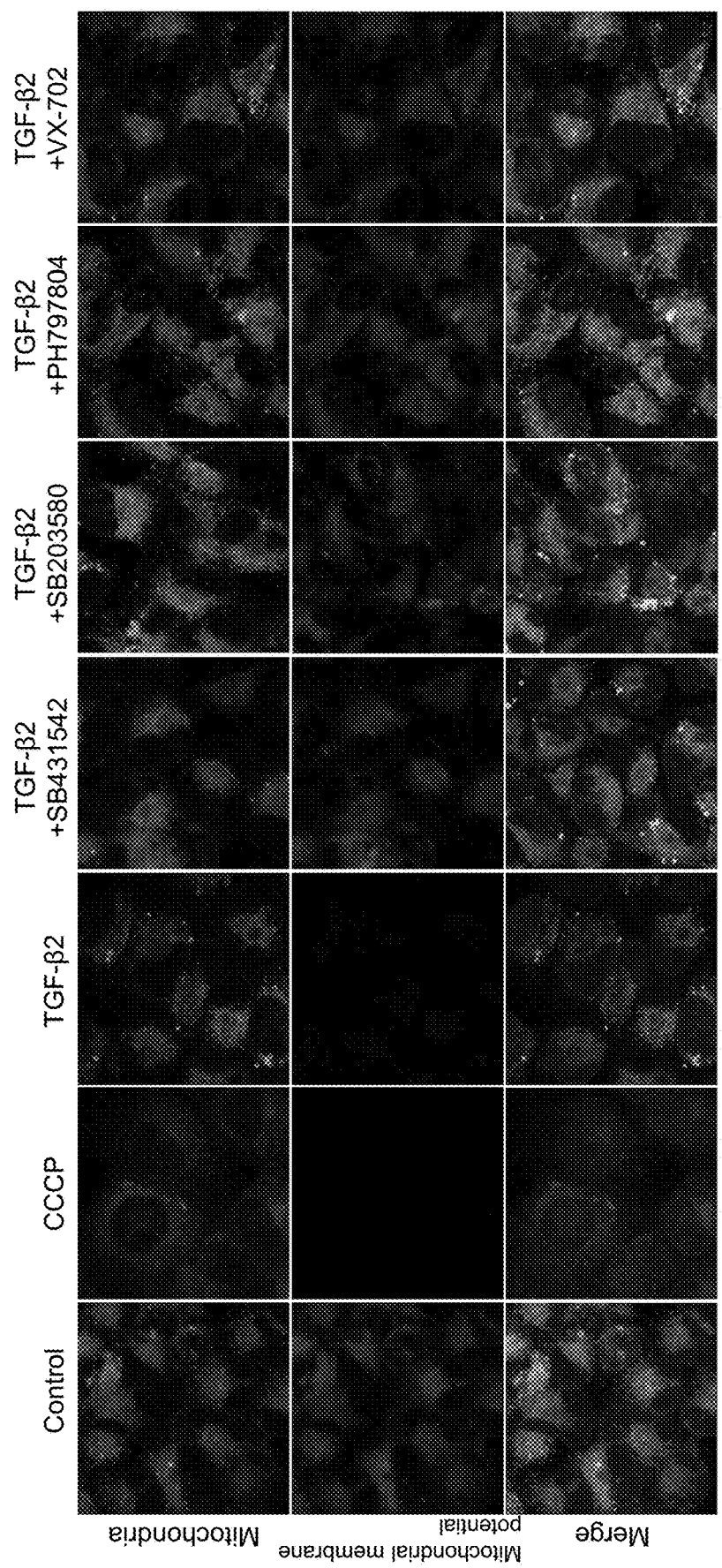
FIG. 5 shows an image stained with a fluorescent dye JC-1. The top row shows mitochondria (green fluorescence), and the middle row shows mitochondrial membrane potential (red fluorescence). The bottom row shows an image created by merging the fluorescence images in the top and middle rows and staining of the nucleus by DAPI (blue). The red stain (middle row) shows mitochondrial membrane potential. The images show, from the left, control, CCCP, TGF-β2, TGF-β2+SB431542, TGF-β2+SB203580, TGF-β2+PH797804, and TGF-β2+VX-702. A p38 MAPK inhibitor suppresses a decrease in mitochondrial membrane potential in a corneal endothelial disorder model of Fuchs' endothelial corneal dystrophy.

Mitochondrial membrane potential was assessed using JC-1 dyes. FIG. 5 shows the results. While green fluorescence indicates mitochondria, and red fluorescence indicates mitochondria membrane potential, lack of red fluorescence indicates that mitochondrial membrane potential is depolarized. Mitochondrial membrane potential was not observed in the group supplemented with the uncoupling agent CCCP due to uncoupling. Similarly, mitochondrial membrane potential was not observed in the TGF-β2 group (in the absence of a p38 MAPK inhibitor), indicating that mitochondrial membrane potential decreases due to a TGF-β2 stimulation. On the other hand, a decrease in mitochondrial membrane potential due to TGF-β2 stimulation was found to be suppressed in the p38 MAPK inhibitor-added groups.

Example 3: Measurement of Mitochondrial Membrane Potential Decreased Cells by Flow Cytometry This Example measured mitochondrial membrane potential decreased cells by flow cytometry in a corneal endothelial disorder model of Fuchs' endothelial corneal dystrophy.

(Materials and Methods)

Figure 6:
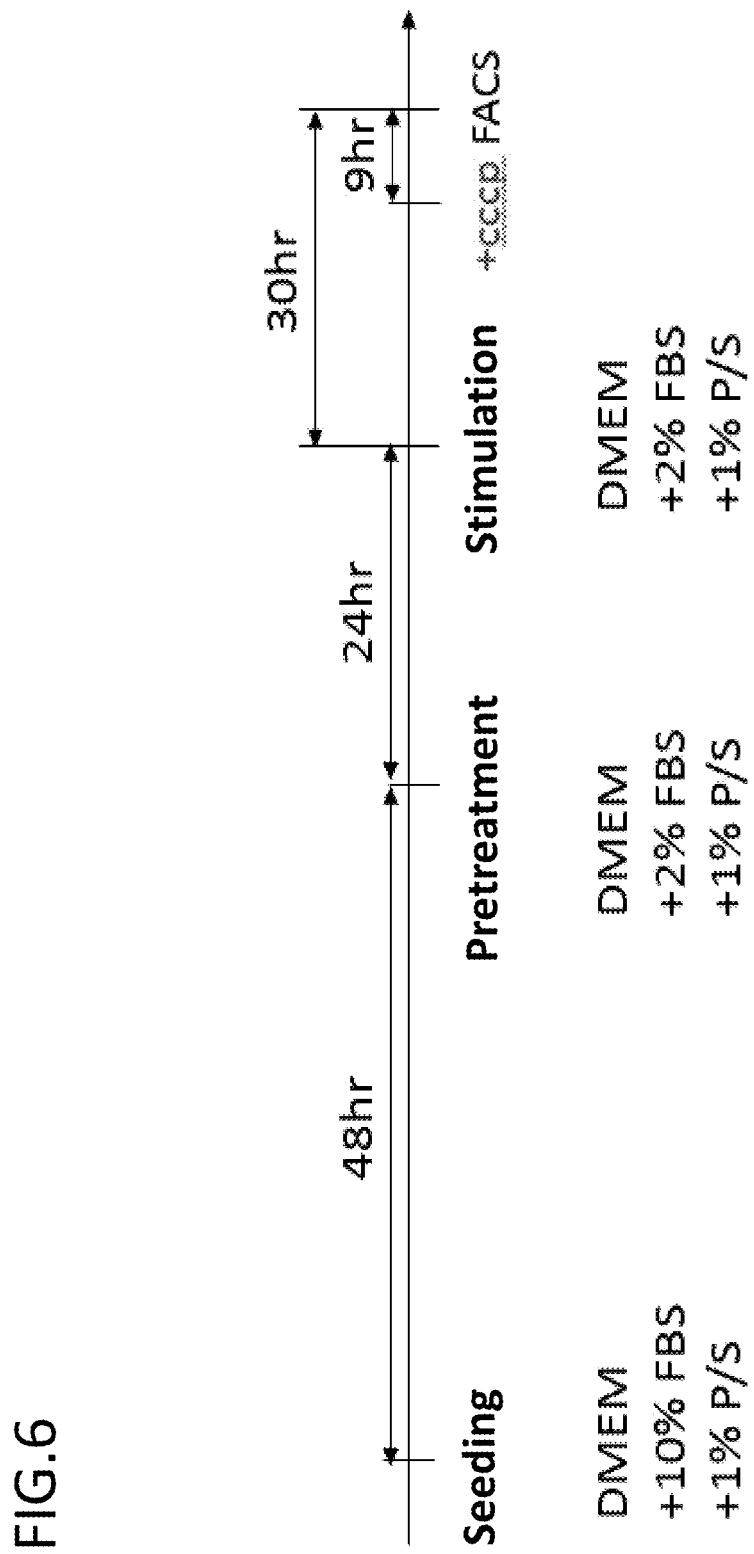
FIG. 6 shows a summary of the protocol of Example 3.

FIG. 6 shows a summary of the protocol of this Example.

The reagents used are the following.

Trypsin-EDTA (200 μl/well)
JC-1 in Assay Buffer (500 μl/well)
1× Assay Buffer (3.5 μl/well)

The medium was removed from a culture dish in which immobilized human corneal endothelial cells were being cultured, and the cells were supplemented with 1×PBS (−) that was preheated to 37° C., and were washed. This was repeated twice. The cells were supplemented again with 1×PBS (−) and incubated for 5 minutes at 37° C. (5% C02). After removing the PBS (−), the cells were supplemented with 0.05% Trypsin-EDTA (Nacalai Tesque, 35554-64) and incubated for 5 minutes at 37° C. (5% $CO_2$). The cells were then suspended in a medium, and collected by centrifugation at 1500 rpm for 3 minutes. DMEM (Nacalai Tesque, 08456-94)+10% FBS (Biowest, S1820-500)+1% P/S (Nacalai Tesque, 26252-94) was used as the medium.

Immobilized human corneal endothelial cells (lot: iFECD3-5) were seeded on a 12-well plate at a ratio of 8×10⁴ cells per well and cultured for 48 hours at 37° C. (5% $CO_2$). DMEM+10% FBS+1% P/S was used as the medium.

After 48 hours, the medium was removed. Each inhibitor was added to culture the cells for 24 hours (pretreatment). DMSO (Dimethyl Sulfoxide Sterile-filtered) (Nacalai Tesque, 13408-64) was added to the control group and the TGF-β2 group. DMEM+2% FBS+1% P/S was used as the medium.

After 24 hours from pretreatment, the CCCP group was supplemented with CCCP (abcam, ab141229), so that the final concentration was 50 μmol/L, and cultured for 9 hours. Samples were prepared by the following procedure after 9 hours only for the CCCP group.

After 24 hours from pretreatment for groups other than the CCCP group, the medium was removed. A medium containing 10 ng/ml of Recombinant Human TGF-β2 (R&D systems, RND302-B2-002) and each inhibitor was added to culture the cells for 30 hours. DMSO was added to the control group. DMEM+2% FBS+1% P/S was used as the medium.

After observation, flow cytometry was performed with JC-1 staining by the following procedure.
1) Sample Preparation The medium was collected to collect free and dead cells. Cells were washed twice with 1×PBS (−). PBS (−) was added again to incubate the cells for 5 minutes at 37° C. (5% $CO_2$). After removing the PBS (−), the cells were supplemented with 0.05% Trypsin-EDTA and incubated for 3 minutes at 37° C. (5% $CO_2$). The cells in the wells were then collected in the medium. The collected cell suspension was then centrifuged for 3 minutes at 1500 rpm. The supernatant was discarded. A mixture of 1× Assay Buffer and Mito-Screen (JC-1) (BD Biosciences, 551302) was added to a tube to incubate the cells at 37° C. (5% $CO_2$) for 15 minutes. 1× Assay Buffer was subsequently added and pipetted, and then the tube was centrifuged for 3 minutes at 1500 rpm. The supernatant was discarded to obtain precipitates. This was repeated twice. 1× Assay Buffer was added again. DMEM+10% FBS+1% P/S was used as the medium.
2) Flow Cytometry The samples prepared above were analyzed using BD Accuri C6 Flow Cytometer (BD).

(Results)

(P38 MAPK Inhibitor Suppresses Decrease in Mitochondrial Membrane Potential in Corneal Endothelial Disorder Model of Fuchs' Endothelial Corneal Dystrophy)

Figure 7:
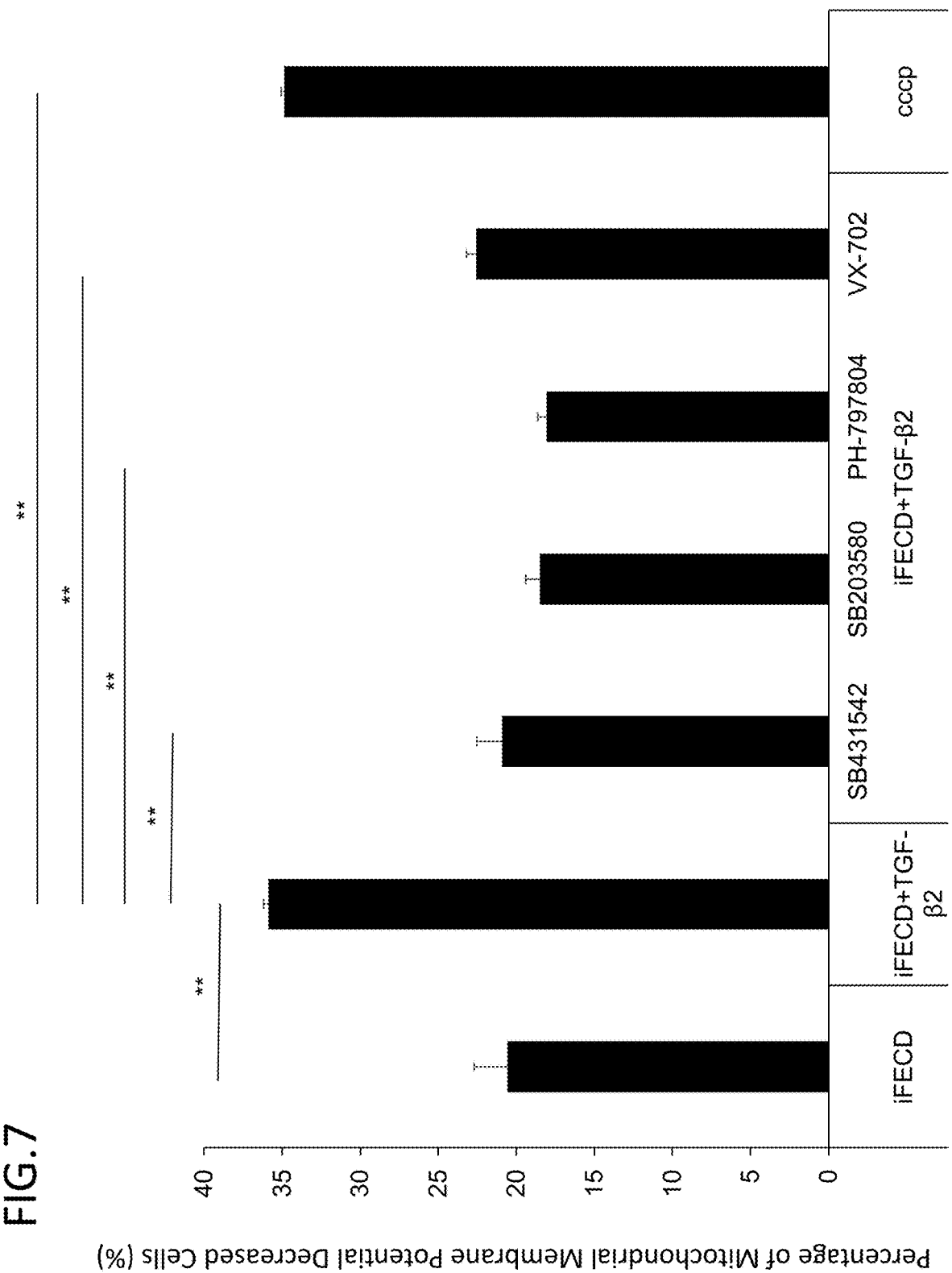
FIG. 7 shows mitochondrial membrane potential measured by flow cytometry. The vertical axis shows the percentage of mitochondrial membrane potential decreased cells (%). The graph shows, from the left, iFECD, iFECD+TGF-β2, iFECD+TGF-β2+SB431543, iFECD+TGF-β2+SB203580, iFECD+TGF-β2+PH-797804, and iFECD+TGF-β2+VX-702. A p38 MAPK inhibitor suppresses a decrease in mitochondrial membrane potential in a corneal endothelial disorder model of Fuchs' endothelial corneal dystrophy. The data is shown as mean±SE and n=3. The p value was calculated using Dunnett's test. ** indicates statistical significance (p<0.01).

FIG. 7 shows the results. The p38 MAPK inhibitor-added groups were found, by flow cytometry, to have a significantly decreased percentage of mitochondrial membrane potential decreased cells compared to the TGF-β2 group. In particular, the SB203580 added group and the PH-797804 added group had a percentage of mitochondrial membrane potential decreased cells that was comparable to or lower than the SB431542 added group.

Example 4: Suppression of Caspase Activation in Corneal Endothelial Disorder Model of Fuchs' Endothelial Corneal Dystrophy This Example studied the suppression of caspase activation by a p38 MAPK inhibitor in corneal endothelial disorder model of Fuchs' endothelial corneal dystrophy.

(Materials and Methods)

Figure 8:
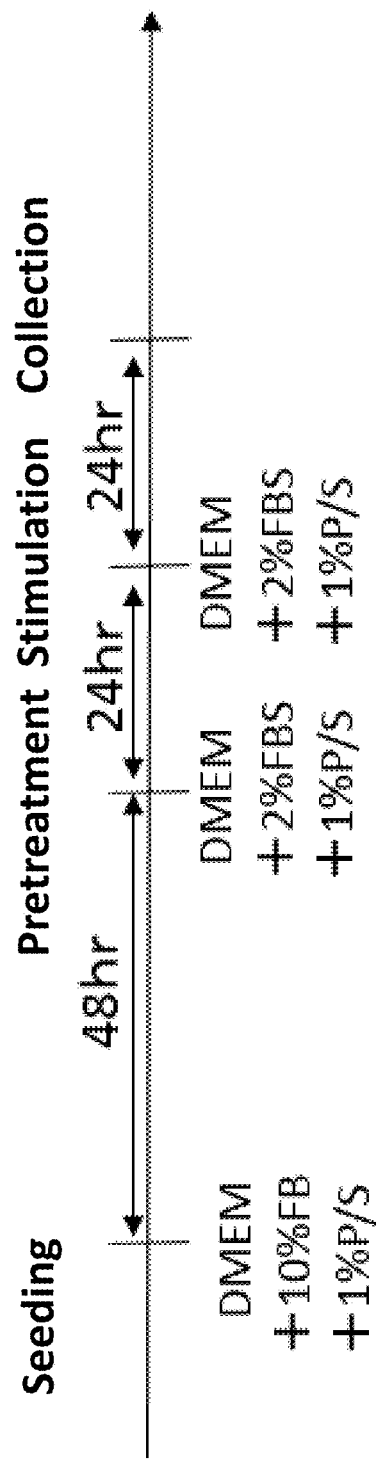
FIG. 8 shows a summary of the protocol of Examples 4 and 5.

FIG. 8 shows a summary of the protocol of this Example.

The medium was removed from a culture dish in which immobilized human corneal endothelial cells were being cultured, and the cells were supplemented with 1×PBS (−) that was preheated to 37° C., and were washed. This was repeated twice. The cells were supplemented again with 1×PBS (−) and incubated for 5 minutes at 37° C. (5% $CO_2$). After removing the PBS (−), the cells were supplemented with 0.05% Trypsin-EDTA (Nacalai Tesque, 35554-64) and incubated for 5 minutes at 37° C. (5% $CO_2$). The cells were then suspended in a medium, and collected by centrifugation at 1500 rpm for 3 minutes. DMEM (Nacalai Tesque, 08456-94)+10% FBS (Biowest, S1820-500)+1% P/S (Nacalai Tesque, 26252-94) was used as the medium.

Immobilized human corneal endothelial cells (lot: iFECD3-5) were seeded on a 12-well plate at a ratio of 8×10⁴ cells per well and cultured for 48 hours at 37° C. (5% $CO_2$). DMEM+10% FBS+1% P/S was used as the medium.

After 48 hours, the medium was removed. Each inhibitor was added to culture the cells for 24 hours. DMSO (Dimethyl Sulfoxide Sterile-filtered) (Nacalai Tesque, 13408-64) was added to the control group and the TGF-β2 group. DMEM+2% FBS+1% P/S was used as the medium.

After 24 hours, the medium was removed. A medium containing 10 ng/ml of Recombinant Human TGF-β2 (R&D systems, RND302-B2-002) and each inhibitor was added to culture the cells for 24 hours. DMSO was added to the control group. DMEM+2% FBS+1% P/S was used as the medium.

After 24 hours, the cell morphology and programmed cell death were observed under a phase differential microscope. After observation, western blot was performed on proteins by the following procedure.
1) Protein Collection The medium was collected on ice to collect free and dead cells. The solution used to wash the cells twice with 1×PBS (−) was also collected. 800 g was centrifuged at 4° C. for 5 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the aforementioned free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of protein.
2) Western Blot 5 μg of the extracted protein was separated by SDS-PAGE and transferred onto a nitrocellulose membrane. A rabbit anti-caspase 3 antibody (Cell Signaling, 9662), rabbit anti-PARP antibody (Cell Signaling, 9542), and mouse anti-GAPDH antibody (MBL, M171-3) were used as the primary antibodies. A peroxidase-labeled anti-rabbit antibody and anti-mouse antibody (GE Healthcare Biosciences, NA934V, NA931V) were used as the secondary antibodies. For the primary antibodies, rabbit anti-caspase 3 antibody: 1000-fold dilution, rabbit anti-PARP antibody: 2000-fold dilution, and mouse anti-GAPDH antibody: 3000-fold dilution, while the secondary antibody was diluted 5000-fold. Chemi Lumi ONE Ultra (nacalai tesque, 11644-40) was used for detection. The detected band strength was analyzed with lumino image analyzer LAS-4000 mini (Fuji Film) and ImageQuant™ software (GE Healthcare).

(Results)

(P38 MAPK Inhibitor Suppresses Caspase Activation in Corneal Endothelial Disorder Model of Fuchs' Endothelial Corneal Dystrophy)

Figure 9:
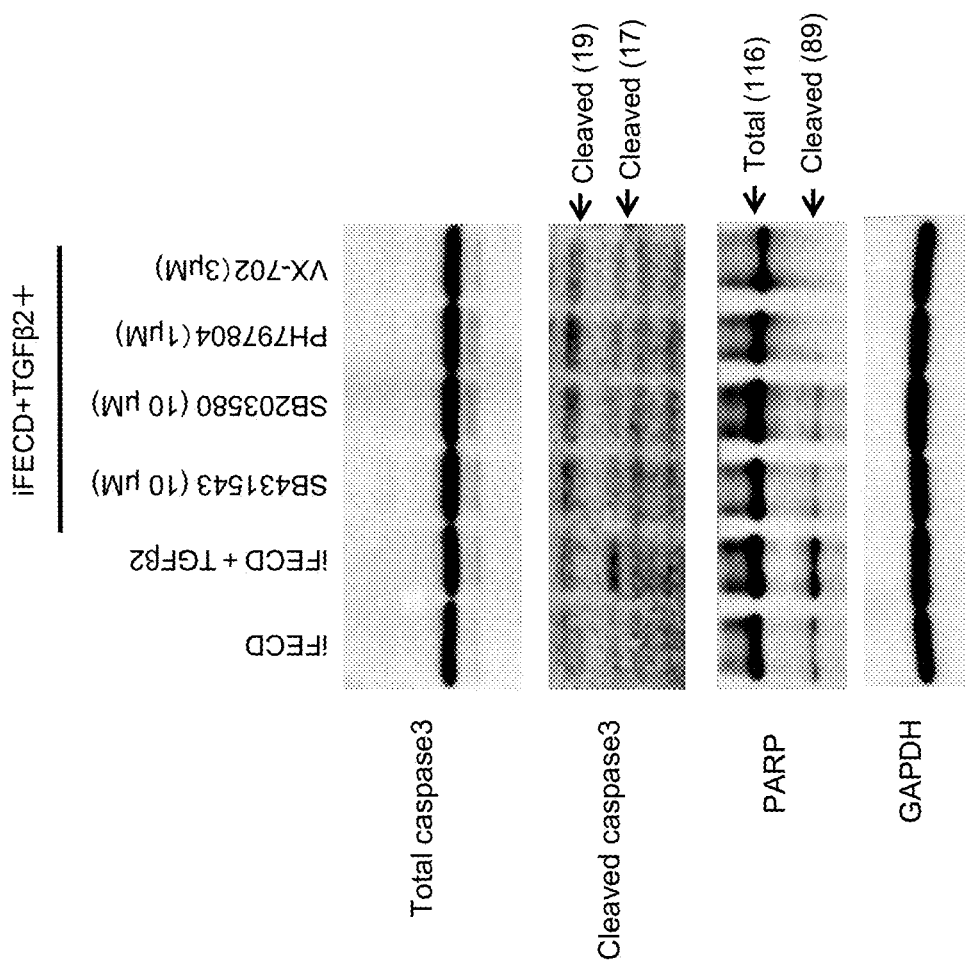
FIG. 9 shows the results of western blot on caspase, PARP, and GAPDH. The picture shows, from the left lane, iFECD, iFECD+TGF-β2, iFECD+TGF-β2+SB431543 (10 μM), iFECD+TGF-β2+SB203580 (10 μM), iFECD+TGF-β2+PH-797804 (1 μM), and iFECD+TGF-β2+VX-702 (3 μM). As shown, when pretreated with a p38 MAPK inhibitor, caspase 3 is cleaved. A p38 MAPK inhibitor suppresses caspase activation in a corneal endothelial disorder model of Fuchs' endothelial corneal dystrophy.

Since mitochondrial abnormalities are understood to be associated with caspase-3 activation, the effect of suppressing caspase activation by a p38 MAPK inhibitor was analyzed. FIG. 9 shows the results. In the absence of a p38 MAPK inhibitor, cleaved caspase-3 (about 17 kDa), which is an active form, was observed. On the other hand, activated form of cleaved caspase-3 was hardly observed in the p38 MAPK inhibitor-added groups, while cleaved caspase 3 of about 19 kDa, which is a non-active form, was observed. Therefore, caspase-3 activation by TGF-β2 stimulation was found to be suppressed by western blot analysis in the p38 MAPK inhibitor-added groups.

Example 5: Suppression of TGF-β Signal in Corneal Endothelial Disorder Model of Fuchs' Endothelial Corneal Dystrophy This Example studied whether a p38 MAPK inhibitor suppresses TGF-β signals in corneal endothelial disorder model of Fuchs' endothelial corneal dystrophy.

(Materials and Methods)

The same procedure as Example 4 was used. However, rabbit anti-Phospho-Smad2 antibody: 1000-fold dilution, rabbit anti-Phospho-Smad3 antibody: 1000-fold dilution, and mouse anti-GAPDH antibody: 3000-fold dilution were used as the primary antibodies.

(Results)

(Cell Damage Suppressing Effect of p38 MAPK Inhibitor in Corneal Endothelial Disorder Model of Fuchs' Endothelial Corneal Dystrophy is not a Result of Suppressing TGF-β Signals)

FIG. 10 shows the results of western blot. In the group supplemented with a TGF-β2 inhibitor SB431542, smad2 and smad3, which are proteins responsible for transmission of information downstream the TGF-β signaling pathway, were not found. Surprisingly, smad2 and smad3 were found in all three p38 MAPK inhibitor-added groups. Therefore, it was elucidated that the cell damage suppressing effect in the p38 MAPK inhibitor-added groups is not a result of suppressing TGF-β signals. In other words, this indicates that a p38 MAPK inhibitor and a TGF-β2 inhibitor have completely different suppression mechanisms and action mechanisms. These results were unexpected.

Example 6: Suppression of Damage to Corneal Endothelial Cells Due to Cryopreservation This Example studied whether a p38 MAPK inhibitor suppresses damage to corneal endothelial cells due to cryopreservation.

(Materials and Methods)

Human corneal endothelial cells cultured in an MSC-CM (MSC cultured medium) were used in the test. The medium was removed from a culture dish in which human corneal endothelial cells were being cultured, and the cells were supplemented with PBS (−) that was preheated to 37° C., and were washed. This was repeated twice. After removing the PBS (−), the cells were supplemented with TrypLE Select (×10) (GIBCO, A12177-01) and incubated for 10 minutes at 37° C. (5% $CO_2$). SB203580 was added to KM BANKER, so that the final concentration was 10 µM. The control group was cryopreserved by supplementing a reagent solvent, dimethyl sulfoxide (DMSO) (Dimethyl Sulfoxide Sterile-filtered; Nacalai Tesque, 13408-64). After 3 days of storage at −80° C., the tube was thawed by being immersed in a 37° C. water bath. After thawing, the sample was washed in a medium. Live and dead cell counts were measured by trypan blue dye exclusion test.

After thawing the cryopreserved cells by adding only DMSO, 10000 cells were seeded in a 96-well plate that was coated with laminin E8. SB203580 (Cayman, catalog number: 13067) was added so that the final concentration was 10 µM upon seeding. DMSO was added to the group to which SB203580 was not added. After 24 hours from seeding, CellTiter-Glo Luminescent Cell Viability Assay (Promega catalog number: G7570) was performed to measure luminescence.

(Results)

FIG. 11 shows the results. When SB203580 was added for cryopreservation, the cell viability was slightly higher immediately after thawing compared to when DMSO was added for cryopreservation. In the SB203580-added group, the cell count was about 1.3 fold compared to the DMSO-added group. This is due to suppression of cell damage to corneal endothelial cells during preservation. Therefore, it was elucidated that a p38 MAPK inhibitor is useful in corneal endothelial cell preservation.

Example 7: Effect of p38 MAPK Inhibitor in Suppressing Cell Damage Due to ER Stress Induced by Thapsigargin Thapsigargin results in unfolded proteins, leading to endoplasmic reticulum (ER) stress. This Example studied the effect of suppressing cell damage induced by thapsigargin in the p38 MAPK inhibitor-added groups.

(Materials and Methods)

The medium was removed from a culture dish in which immobilized human corneal endothelial cells were being cultured, and the cells were supplemented with 1×PBS (−) that was preheated to 37° C., and were washed. This was repeated twice. The cells were supplemented again with 1×PBS (−) and incubated for 5 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium. Immobilized human corneal endothelial cells (lot: iHCEC1-1) were seeded on a 12-well plate at a ratio of $8\times10^4$ cells per well and cultured for 48 hours at 37° C. (5% $CO_2$) while using DMEM+10% FBS+1% P/S as the medium. The medium was then removed and each inhibitor was added to culture the cells for 24 hours using DMEM+2% FBS+1% P/S as the medium. The medium was then removed. A medium (DMEM+2% FBS+1% P/S) containing 20 µM of thapsigargin (Wako, 209-17281) and each inhibitor was added to culture the cells for 3 hours. Then, the cell morphology and apoptosis were observed under a phase differential microscope. After observation, western blot was performed on proteins by the following procedure.

1) Protein Collection

The medium was collected on ice to collected free and dead cells. The solution used to wash the cells twice with 1×PBS (−) was also collected, which was centrifuged (4° C., 800 g) for 5 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the aforementioned free and dead cells were also subsequently suspended together for extraction. The collected solution was pulverized three times for 30 seconds in cold water with a sonication device (BIORUPTOR, TOSHO DENKI) and then centrifuged for 10 min (4° C., 15000 rpm) to collect the supernatant of protein.

2) Western Blot

10 μg of the extracted protein was separated by SDS-PAGE and transferred onto a nitrocellulose membrane. A rabbit anti-caspase 3 antibody (Cell Signaling, 9662) diluted 1000-fold, rabbit anti-PARP antibody (Cell Signaling, 9542) diluted 2000-fold, and mouse anti-GAPDH antibody (MBL, M171-3) diluted 3000-fold were used as the primary antibodies. A peroxidase-labeled anti-rabbit antibody and anti-mouse antibody (GE Healthcare Biosciences, NA931V, NA934V) diluted 5000-fold were used as the secondary antibodies. Chemi Lumi ONE Ultra (nacalai tesque, 11644-40) was used for detection. The detected band strength was analyzed with lumino image analyzer LAS-4000 mini (Fuji Film) and ImageQuant™ software (GE Healthcare).

(Results)

FIGS. 12 and 13 show the results. In the absence of a p38 MAPK inhibitor in immobilized human corneal endothelial cells, significant damage to the cells was observed when stimulated by thapsigargin. On the other hand, suppression of damage to the corneal endothelial cells was observed when pretreated with a p38 MAPK inhibitor. Further, in the absence of a p38 MAPK inhibitor in immobilized human corneal endothelial cells, cleaved caspase-3 (about 17 kDa), which is an active form, was observed when stimulated by thapsigargin. On the other hand, activated form of cleaved caspase-3 was hardly observed in the p38 MAPK inhibitor-added groups. In view of the above, a p38 MAPK inhibitor was found to suppress apoptosis due to ER stress induced by thapsigargin by western blot analysis.

Example 8: Effect of p38 MAPK on Suppression of CHOP Expression Due to TGFβ

Since cell death due to ER stress is understood to be associated with the activation of an apoptosis inducing transcription factor CHOP, this Example analyzed the effect of suppressing CHOP activation by a p38 MAPK inhibitor.

(Materials and Methods)

Cells were cultured in the same manner as Example 7, except 10 ng/ml of Recombinant Human TGF-β2 (R&D systems, RND302-B2-002) was used in place of 20 μM of thapsigargin. Protein collection and western blot were also performed in the same manner as Example 7. A mouse anti-CHOP antibody (Cell Signaling, 2895) diluted 1000-fold and mouse anti-GAPDH antibody (MBL, M171-3) diluted 3000-fold were used as the primary antibodies. A peroxidase-labeled anti-mouse antibody (GE Healthcare Biosciences, NA934V) diluted 5000-fold was used as the secondary antibodies.

(Results)

(P38 MAPK Inhibitor Suppresses CHOP Activation in Corneal Endothelial Disorder Model of Fuchs' Endothelial Corneal Dystrophy)

FIG. 14 shows the results. Expression of CHOP was observed when immobilized human corneal endothelial cells were stimulated by TGF-β2 in the absence of a p38 MAPK inhibitor. On the other hand, expression of CHOP was hardly observed when stimulated with TGF-β2 in the p38 MAPK inhibitor-added groups. Therefore, a p38 MAPK inhibitor was found to suppress CHOP activation, which is involved with ER stress. This suggests that a p38 MAP kinase inhibitor can suppress ER stress due to TGF-β.

Example 9: Formulation Example: Cornea Preservation Solution Containing p38 MAPK Inhibitor As a formulation example, this Example manufactures a cornea preservation solution containing a p38 MAPK inhibitor as follows.

The following preservation solutions are prepared by a conventional method.

| | |
|---|---|
| SB203580 | 0.37743 mg |
| Optisol-GS (Bausch-Lomb) | optimal dose |
| Total amount | 100 mL |

SB203580 manufactured by CALBIOCHEM can be used as the SB203580.

Example 10: Preparation Example for Eye Drop

The composition of test substance at each concentration is shown below.

| | |
|---|---|
| SB203580 or suitable concentration of other p38 MAPK inhibitors | 1 mM (377.43 mg) |
| Sodium chloride | 0.85 g |
| Sodium dihydrogen phosphate dehydrate | 0.1 g |
| Benzalkonium chloride | 0.005 g |
| Sodium hydroxide | Optimal dose |
| Purified water | Optimal dose |
| Total amount | 100 mL (pH 7.0) |

The concentration may be diluted using a base consisting of the following.

| | |
|---|---|
| Sodium chloride | 0.85 g |
| Sodium dihydrogen phosphate dehydrate | 0.1 g |
| Benzalkonium chloride | 0.005 g |
| Sodium hydroxide | Optimal dose |
| Purified water | Optimal dose |
| Total amount | 100 mL (pH 7.0) |

A commercially available substance that is compatible with the Japanese Pharmacopoeia or an equivalent product thereof or the like can be used as each component other than the active ingredient.

Example 11: Therapy Example

The present invention is used when diagnosed with Fuchs' endothelial corneal dystrophy or a similar corneal endothelial disease (specific examples thereof include 1) observation of guttae formation, hypertrophy of the Descemet's membrane, corneal epithelial edema, or edema of the corneal stroma by slit-lamp microscopy, 2) observation of images of guttae or corneal endothelial disorder with a specular microscope, 3) observation of corneal edema with a Pentacam, OCT, ultrasonic corneal thickness measuring apparatus, or the like, and 4) when determined as high risk by genetic diagnosis). Examples of expected use include eye drops, injection into the anterior chamber, administration using controlled-release agent, intravitreal injection, subconjunctival injection, and the like.

In this case, eye drops manufactured in Example 10 can be used.

Injection into the anterior chamber, administration using controlled-release agent, intravitreal injection, and subconjunctival injection are prepared using methods that are known in the art. Such injection formulations can be prepared to be about 1 mM, which is about the same as an eye drop, but the concentration can be appropriately increased or decreased.

As disclosed above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein. The present application claims priority to Japanese Patent Application No. 2015-251786 filed on Dec. 24, 2015. The entire content thereof is incorporated herein by reference.

INDUSTRIAL APPLICABILITY

The present invention provides a medicament for use in treating or preventing a corneal endothelial disorder due to a transforming growth factor-β (TGF-β) signal, mitochondrial abnormality, and/or endoplasmic reticulum (ER) associated stress, comprising a p38 MAP kinase inhibitor, especially a medicament for use in treating or preventing a corneal endothelial disorder in Fuchs' endothelial corneal dystrophy. The present invention provides a technique available to industries (pharmaceutical or the like) involved in techniques associated with formulation or the like based on such a technique.

The invention claimed is:

1. A method for treating a corneal endothelial condition, disorder, or disease due to a transforming growth factor-β (TGF-β) signal in corneal endothelial cells in a subject in need thereof, comprising administering to the subject having the corneal endothelial condition, disorder, or disease due to a TGF-β signal in corneal endothelial cells an effective amount of a p38 MAP kinase inhibitor to treat the corneal endothelial condition, disorder, or disease, wherein the subject has not undergone a corneal transplant, wherein the condition, disorder, or disease is a condition, disorder, or disease in Fuchs' endothelial corneal dystrophy, and wherein the p38 MAP kinase inhibitor comprises 4-(4-fluorophenyl)-2-(4-methylsulfinylphenyl)-5-(4-pyridyl)-1H-imidazole (SB-203580).

2. The method of claim 1, wherein the condition, disorder, or disease is associated with a TGF-β signal.

3. The method of claim 1, wherein the p38 MAP kinase inhibitor prevents the progression of Fuchs' endothelial corneal dystrophy by suppressing a decrease in mitochondrial membrane potential of corneal endothelial cells in Fuchs' endothelial corneal dystrophy.

4. The method of claim 1, wherein the p38 MAP kinase inhibitor comprises 4-(4-fluorophenyl)-2-(4-methylsulfinylphenyl)-5-(4-pyridyl)-1H-imidazole (SB203580) at a concentration of about 3 µM to about 30 µM.

* * * * *